US008034617B2

(12) United States Patent
Aerts et al.

(10) Patent No.: US 8,034,617 B2
(45) Date of Patent: Oct. 11, 2011

(54) CELL CULTURE IN CULTURE MEDIA FREE OF COMPONENTS OF ANIMAL ORIGIN

(75) Inventors: Brigitte Ghislaine Louise Aerts, Rixensart (BE); Yves Jules Maurice Ghislain, Rixensart (BE); Marie-Monique Jane Gonze, Rixensart (BE); Isabelle Solange Lucie Knott, Rixensart (BE); Carine Maggetto, Rixensart (BE)

(73) Assignee: Glaxosmithkline Biologicals S.A., Rixensart (BE)

( * ) Notice: Subject to any disclaimer, the term of this patent is extended or adjusted under 35 U.S.C. 154(b) by 1046 days.

(21) Appl. No.: 10/547,804

(22) PCT Filed: Mar. 1, 2004

(86) PCT No.: PCT/EP2004/002067
§ 371 (c)(1),
(2), (4) Date: Sep. 2, 2005

(87) PCT Pub. No.: WO2004/078955
PCT Pub. Date: Sep. 16, 2004

(65) Prior Publication Data
US 2006/0183224 A1    Aug. 17, 2006

(30) Foreign Application Priority Data
Mar. 3, 2003    (GB) .................................. 0304799.0

(51) Int. Cl.
*C12N 5/00* (2006.01)
(52) U.S. Cl. ......................... 435/395; 435/404; 435/405
(58) Field of Classification Search .................. None
See application file for complete search history.

(56) References Cited

U.S. PATENT DOCUMENTS

| 5,712,163 | A | | 1/1998 | Parenteau et al. | |
|---|---|---|---|---|---|
| 6,103,529 | A | * | 8/2000 | Price et al. | 435/404 |
| 6,406,909 | B1 | * | 6/2002 | Shibuya et al. | 435/404 |
| 2002/0192805 | A1 | * | 12/2002 | Harris | 435/267 |

FOREIGN PATENT DOCUMENTS

| EP | 513738 | 11/1992 |
|---|---|---|
| EP | 1221476 | 7/2002 |
| WO | WO 94/06446 | 3/1994 |
| WO | WO 95/24468 | 9/1995 |
| WO | WO 9615231 | 5/1996 |
| WO | WO 9804680 | 2/1998 |
| WO | W09815614 | 4/1998 |
| WO | WO 9859035 | 12/1998 |
| WO | WO 9921969 | 5/1999 |
| WO | WO 9947648 | 9/1999 |
| WO | WO 9957246 | 11/1999 |
| WO | WO0003000 | 1/2000 |

OTHER PUBLICATIONS

Groves et al, "cAMP signaling can antagonize potent glucocortoid post-transcriptional inhibition of stanniocalcin gene expression" Journal of Endocrinology, 2001, vol. 171, pp. 499-516.*

Phelan, Mary C. "Basic Techniques for Mammalian Cell Tissue Culture" Current Protocols in Cell Biology, 1998, John Wiley and Sons, Inc; pp. 1.1.1-1.1.10.*
Bettger et al, Proc Natl Acad Sci. USA, 1981, vol. 78, No. 9, pp. 5588-5592.*
Merten et al, Cytotechnology, 1999, vol. 30, pp. 191-201.*
R.I. Freshney, Culture of Animal Cells: A manual of basic technique ($4^{th}$ edition). New York: Wiley-Liss, Inc, 2000. p. 178.*
Cruz, H.J., et al., "Cell-dislodging methods under serum-free conditions", *Applied Microbiology and Biotechnology*, vol. 47(5), pp. 482-488 (1997).
Liener, I.E., "Ficin", *Methods in Enzymology*, vol. 19, pp. 261-273 (1970).
Grinnell, F., et al., "Initial Adhesion of Human Fibroblasts in Serum-Free Medium: Possible Role of Secreted Fibronectin", *Cell*, vol. 17, pp. 117-129 (1979).
Walthall, B.J., et al., "Multiplication of Human Diploid Fibroblasts in a Synthetic Medium Supplemented with EGF, Insulin, and Dexamethasone", *Experimental Cell Research*, vol. 134, pp. 303-311 (1981).
Kan, M., et al, "In Vitro Proliferation and Lifespan of Human Diploid Fibroblast in Serum-Free BSA-Containing Medium", *Journal of Cellular Physiology*, vol. 111, pp. 155-162 (1982).
Brocklehurst K., et al., "Cysteine proteinases", *New Comprehensive Biochemistry*, vol. 16, pp. 39-158 (1987).
Greer, J., "Comparative Modeling Methods: Application to the Family of the Mammalian Serine Proteases", *Proteins: Structure, Function and Genetics*, vol. 7, pp. 317-334 (1990).
Sali, A., et al., "Definition of General Topological Equivalence in Protein Structures", *Journal Mol. Biol.*, vol. 212, pp. 403-428 (1990).
Chandler J.P., "Cultivation of mammalian cells in serum-free medium", *Am Biotechol Lab*, vol. 8, (1990). pp. 18, 20-28.
Wistrom, C., et al., "Long-Term Growth of Diploid Human Fibroblasts in Low Serum Media", *Experimental Gerontology*, vol. 25(2), pp. 97-105 (1990).
Forestell, S.P., et al., "The Extended Serial Subculture of Human Diploid Fibroblasts on Microcarriers Using a New Medium Supplement Formulation", *Biotechnology and Bioengineering*, vol. 40(9), pp. 1039-1044 (1992).
Koller, M.R., "Cell Adhesion in Animal Cell Culture: Physiological and Fluid-Mechanical Implications", *Bioprocess Technology*, vol. 60, pp. 61-110 (1995).

(Continued)

*Primary Examiner* — Allison Ford
(74) *Attorney, Agent, or Firm* — Convergent Law Group LLP

(57) ABSTRACT

The present invention relates to a process for animal, preferably human, diploid anchorage-dependent cell culture, in the absence of exogenous components of primary animal origin, and to a cell culture medium substantially free of exogenous components of primary animal origin suitable for carrying out said process. In particular the invention concerns a cell culture medium which comprises at least one, more preferably several, exogenous animal-free growth factors. The present invention also relates to a process for cultivating animal, preferably human diploid anchorage-dependent cells in a medium according to the invention, involving the use of a trypsin substitute of non-animal origin for passaging cells. The invention further relates to a process for producing viruses, viral vaccines and the like.

36 Claims, 7 Drawing Sheets

OTHER PUBLICATIONS

Figure 1:
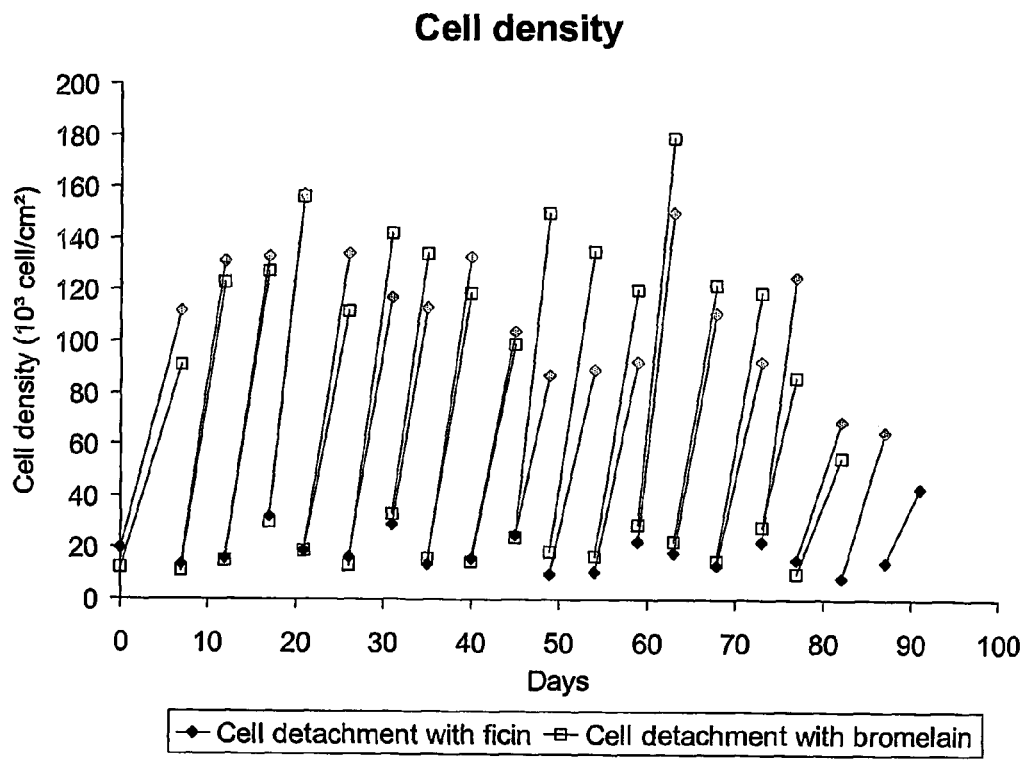

Scröder, M., et al., "A protein-free solution as replacement for serum in trypsinization protocols for anchorage-dependent cells", *Methods in Cell Science*, vol. 19, pp. 137-147 (1997).

Merten, O.-W., "Safety Issues of Animal Products Used in Serum-Free Media", *Biol Stand.*, vol. 99, pp. 167-180 (1999).

Merten, O.-W., "Safety for vaccine(e)s", *Cytotechnology*, vol. 34, pp. 181-183 (2000).

Hagen, et al., "Development, preparation, and testing of VAQTA®, a highly purified hepatitis a vaccine", *Bioprocess Engineering*, vol. 23, pp. 439-449 (2000).

Merten, O.-W., "Development of Serum-Free Media for Cell Growth and Production of Viruses/Viral Vaccines—Safety Issues of Animal Products Used in Serum-Free Media", *Dev Biol Stand.*, vol. 111, pp. 233-257 (2002).

Rubin, H., "The disparity between human cell senescence in vitro and lifelong replication in vivo", *Nature Biotechnology*, vol. 20, pp. 675-681 (2002).

Jayme, D.W., et al., "Media formulation options and manufacturing process controls to safeguard against introduction of animal origin contaminants in animal cell culture", *Cytotechnology*, vol. 33, 27-36 (2000).

Jayme, D.W., "An Animal Origin Perspective of Common Constituents of Serum-Free Medium Formulations", *Dev Biol Stand.*, vol. 99, 181-187 (1999).

Miller W.A., et al., "Enzyme Separation Techniques for the Study of Growth of Cells from Layers of Bovine Dental Pulp", In vitro, vol. 12, 580-588 (1976).

Ben-Nathan, D., et al., "RDB—A New Product of Plant Origin for Cell Culture Dispersion", *Dev Biol. Stand.*, vol. 60, 467-473 (1985).

* cited by examiner

CELL CULTURE IN CULTURE MEDIA FREE OF COMPONENTS OF ANIMAL ORIGIN

The present invention relates to a process for animal, such as mammalian cell culture, in particular for animal, such as mammalian or preferably human, diploid anchorage-dependent cell culture, in the absence of exogenous components of primary animal origin, and to a cell culture medium substantially free of exogenous components of primary animal origin suitable for carrying out said process. In particular the invention concerns a cell culture medium which comprises at least one, more preferably several, exogenous animal-free growth factors. Such a medium is particularly adapted for culturing animal, such as mammalian, or preferably human diploid anchorage-dependent cells, e.g. with equivalent performance to that of a basal medium for the cell type supplemented with an appropriate serum. The present invention also relates to a process for cultivating animal, such as mammalian, or preferably human diploid anchorage-dependent cells in a medium according to the invention, involving the use of a trypsin substitute of non-animal origin for passaging cells. The invention further relates to a process for producing viruses, viral vaccines and the like.

BACKGROUND OF THE INVENTION

Anchorage-dependent cells, especially diploid anchorage-dependent cells are used in a wide range of processes: for the production of health care products such as vaccines and recombinant proteins in large-scale bioprocesses, for the generation of artificial tissues used in the treatment of human injuries, for experimental investigations, for in vitro toxicology, for screening and testing of new drugs, etc.

Conventionally, anchorage-dependent cells are cultured in media containing serum or other animal-origin components as substitutes for the serum, such as bovine serum albumin (BSA) or protein hydrolysates. Serum or animal-origin components are also used during cell subcultivation and in cell cryopreservation. Serum is a major source for metabolites, hormones, vitamins, iron (transferrin), transport proteins, attachment factors (e.g. fibronectin), spreading and growth factors. It is required for the growth of many animal cells culture in vitro. In addition, serum acts as buffer against a variety of perturbation and toxic effects such as pH change, presence of heavy metal ions, proteolytic activity, or endotoxins. Albumin is the major protein component of serum and exerts several effects which contribute to the growth and maintenance of cells in culture: it acts as a carrier protein for a range of small molecules and as a transporter for fatty acids which are essential for cells but are toxic in the unbound form.

Diploid anchorage-dependent cells are routinely grown on plastic surface, glass surface or microcarriers. The cells attach and spread out by attachment factors such as fibronectin (F. Grinnel & M. K. Feld Cell, 1979, 17, 117-129). Trypsin is one of the most common animal-derived component used for cell detachment during cell passaging (M. Schröder & P. Friedl, Methods in Cell Science, 1997, 19, 137-147; O. W. Mertens, Dev Biol Stand., 1999, Vol 99, pp 167-180). It must be inhibited by serum or soybean trypsin inhibitor after cell detachment in order to avoid cell damages. After detachment, cells are seeded at low density on a new surface where they can multiply and form a confluent cell layer before the next subcultivation. The purpose of passaging adherent cells is to multiply and obtain a sufficient amount of cells to carry out the aforementioned processes.

There are various disadvantages linked to the use of serum and of animal-derived components in these processes, mainly their cost, the batch to batch variability in their composition, their association with a higher contamination risk by adventitious agents, and the subsequent difficulties encountered in downstream processing (e.g. purification to get rid of the serum-proteins or of the introduced animal-derived proteins). Furthermore, as said above, it is reported that serum-free media are not suitable for anchorage dependent diploïd cells (O. W. Mertens, Dev Biol Stand., 1999, Vol 99, pp 167-180; O. W. Merten, Dev. Biol. 2002, 101,233-257).

A number of low-serum or serum-free medium formulations have been developed for anchorage-dependent cell culture, in particular for diploid anchorage-dependent cell culture (M. Kan & I. Yamane, Journal of Cellular Physiology, 1982, 111, 155-162; S. P. Forestell et al. Biotechnology and Bioenineering, 1992, Vol 40, pp 1039-1044). Attempts made with such media have not been satisfactory, mainly because diploid anchorage-dependent cell, which are not transformed, would need rather complex serum-free media supplemented with several growth factors and hormones, and also because production processes generally for such cells make use of serum at least during the biomass production phase (O. W. Merten, Dev. Biol. 2002, 101, 233-257). Furthermore, these media still contain components of animal origin, like BSA, protein hydrolysates, growth factors, transport proteins, amino acids, vitamins, etc. Very few attempts have been made to develop media formulations for anchorage-dependent cells which are totally free of components of animal origin. Formulations which are mostly animal-free are reported not to be able to sustain a cell growth rate equivalent to what is observed with serum and to only allow a few subcultivation steps before an early senescence is observed (B. J. Walthall & R. Ham Experimental Cell Research (1981) 134 303-311). Furthermore, primary cell cultures from anchorage-dependent cells almost always involve disaggregation of cell layers or tissue using a protease, mainly a serine-protease, of animal origin, thereby involving a risk of contaminating the cell culture with adventitious virus and causing unacceptable variability in cell growth due to batch to batch variation in the enzymatic activity of the protease. For example, the use of porcine/bovine trypsin in passaging anchorage-dependent cell cultures is a well-known technique (O. W. Mertens, Cytotechnology, 2000, 34, 181-183).

There exists a need therefore, in the field of diploid anchorage-dependent cell culture, to develop a cell culture medium which is substantially free from, preferably totally devoid of, animal-derived components, and is suitable for carrying a process for diploid anchorage-dependent cell culture with equivalent performances to that of a basal medium for the cell type supplemented with an appropriate serum, in terms of, for example, cell growth rate, senescence, cell morphology, viral or protein production, to these obtained with serum-containing processes.

STATEMENT OF THE INVENTION

It has now been found that the use of a cell culture medium substantially free from exogenous components of primary animal origin and comprising at least one exogeneous growth factor of non-animal secondary origin, can advantageously replace conventional culture media and serum-free media which are known to contain components from exogeneous primary and/or secondary animal origin.

It has also been found that a cell culture process, involving the use of said culture medium and further comprising passaging animal, such as mammalian, or preferably human cells, preferably anchorage-dependent cells one or more times in the presence of a protease substitute which is not from animal origin, can also be carried out with a level of performance equivalent to that obtained with the classical process carried out using a basal medium for the cell type supplemented with an appropriate serum.

Accordingly, in a first aspect, the present invention relates to a cell culture medium substantially free from, preferably devoid of, exogenous components of primary animal origin, comprising at least one, preferably more than one, exogenous growth factor of non-animal secondary origin selected from the list consisting of EGF, FGF, tri-iodo-L tyronine and hydrocortisone and at least one of IGF-1 and/or Insulin of non-animal secondary origin. Suitably said culture medium is adapted for the cultivation of animal, such as mammalian, or preferably human anchorage-dependent cells, preferably diploid cells, e.g. with equivalent performance to that of a basal medium for the cell type supplemented with an appropriate serum.

Optionally the culture medium according to the invention additionally comprises a protein hydrolysate of non-animal origin. Preferably the protein hydrolysate is present. Suitably the protein hydrolysate is a wheat hydrolysate.

Further the present invention relates to the use of said medium for the cultivation of animal, such as mammalian, or preferably human anchorage-dependent cells, preferably anchorage-dependent diploid cells, with equivalent performance to that obtained with a basal medium for the cell type supplemented with an appropriate serum.

We have surprisingly determined that the medium according to the invention is especially adapted for culturing animal, such as mammalian, or preferably human anchorage-dependent cells, especially anchorage-dependent diploid cells, e.g. with equivalent performance (e.g. cell growth rate, senescence, cell morphology, viral or protein production) to that obtained with a basal medium for the cell type, supplemented with animal-derived components such as serum.

The invention thus particularly relates to a process for producing animal, such as mammalian, or preferably human anchorage-dependent cells, preferably diploid cells, in a cell culture medium according to the invention, said process comprising:
a) seeding the cells in said culture medium as herein defined, and letting the cells adhere to the substrate;
b) harvesting the conditioned medium resulting from step a), and detaching the cell layer from its substrate and dissociating cells with a protease of non-animal origin, thereby forming a cell suspension;
c) inoculating in said culture medium the suspension of cells of step b), in a culture device comprising an adhesion support allowing cell attachment; and
d) growing the cells in the culture medium.

Steps b) to d) can be repeated several times.

Optionally, the process further comprises the step of freezing the cells harvested from the step b), to produce a cell bank.

It has also been found that said process for producing cells does not require any adaptation steps before cultivating cells in the medium free from exogenous animal-derived components and that the senescence of the cells is not affected by the absence of this adaptation step.

It is thus another aspect of the invention to provide for a cell line, in particular for a animal, such as mammalian or preferably human diploid anchorage-dependent cell line, adapted for growth in a culture medium according to the invention, and in particular to provide for a cell line, in particular for a animal, such as mammalian or preferably human diploid anchorage-dependent cell line, adapted for production of a biologically active product, preferably a virus, in particular a live virus for use as a vaccine.

The invention also relates to a process for the production of viruses in animal, such as mammalian or preferably human anchorage-dependent cells in a cell culture medium suitable for viral production, said medium being devoid of components of primary animal origin, and comprising at least one exogenous growth factor of non-animal secondary origin and, optionally, one protein hydrolysate of non-animal origin, said process comprising the steps of:
a) infecting the cells with the virus
b) propagating the viruses, and
c) harvesting the viruses.

The process may include submitting the harvested virus to one or more purification steps. The virus may be suitably formulated as a vaccine, with a pharmaceutically acceptable carrier, excipient and/or adjuvant.

DETAILED DESCRIPTION

In a particularly preferred embodiment the cell culture medium according to the invention is substantially free from, preferably totally devoid of, exogenous components of primary animal origin, preferably it is free from exogenous animal-derived components of primary and secondary animal origin. Suitably said medium is adapted for culturing animal, such as mammalian, or preferably human anchorage-dependent cells, especially anchorage-dependent diploid cells, e.g. with a performance which is equivalent, in terms of, for example, cell growth rate, cell morphology, senescence or viral production, to that obtained with a basal medium for the cell type and supplemented with an appropriate serum. For example a basal medium for animal, such as mammalian or preferably human cells can be found in the ATCC catalog, and examples of basal media for given cell types are additionally given in Table 1. The serum used for comparative purposes is typically a bovine serum, especially fetal bovine serum. Thus equivalence is best assessed in comparison with a basal medium according to Table 1, and containing bovine serum, typically at a concentration of 10% v/v.

TABLE 1

| Cell type | Basal medium* | Serum |
|---|---|---|
| MRC-5 (ATCC CCL-171) | Minimum essential medium (MEM-Eagle) | Fetal bovine serum, 10% |
| AGMK | Minimum essential medium (MEM-Eagle) or M199 | Fetal bovine serum, 10% |
| VERO (ATCC CCL-81) | Minimum essential medium (MEM-Eagle) or M199 | Fetal bovine serum, 10% |
| MDCK (ATCC CCL-34) | Minimum essential medium (MEM-Eagle) | Fetal bovine serum, 10% |
| CHO (ATCC CCL-61) | ATCC medium Ham's F12K | Fetal bovine serum, 10% |
| WI-38 (ATCC CCL-75) | Minimum essential medium (MEM-Eagle) | Fetal bovine serum, 10% |
| DBS-FRhL-2 (ATCC CCL-160) | Minimum essential medium (MEM-Eagle) | Fetal bovine serum, 10% |
| MRC-9 (ATCC CCL-212) | Minimum essential medium (MEM-Eagle) | Fetal bovine serum, 10% |
| IMR-90 (female, ATCC CCL-186) | Minimum essential medium (MEM-Eagle) | Fetal bovine serum, 10% |
| IMR-91 (male, National Insitute of Aging - NIA) | Minimum essential medium (MEM-Eagle) | Fetal bovine serum, 15% |

*basal medium supplemented with amino acids and vitamins according to the ATCC or NIA instructions By "cell growth rate" is meant the average rate at which the cells grow between their thawing from a cell bank and their senescence. It is expressed in Population Doubling (PD)/day and obtained by calculating the ratio of the number of Population Doubling, observed between the cell thawing and their senescence, to the time (expressed in days) elapsed between the cell thawing and their senescence. An equivalent cell growth rate according to the invention means a cell growth rate which is at least 80%, preferably 90%, more preferably at least 95% or above, of that obtained with the cells cultivated in a basal medium for the cell type and supplemented with an appropriate serum, usually bovine serum at a 10% concentration (used as a control). Still most preferred is a cell growth rate which is higher than that obtained with cells cultivated in a serum-containing medium.

By "cell morphology" is meant the morphology of the cells as assessed by optical microscopy. An equivalent performance in terms of morphology means that the cells have retained the morphology they showed when cultivated in the presence of bovine serum. As an example, MRC-5 cells will have retained their fibroblastic nature following cultivation in a medium according to the present invention.

By "senescence" is meant the loss of replicative capacity of the cells observed after a uniform, fixed number of population doubling (population doubling level, PDL), commonly termed the Hayflick limit (Harry Rubin, Nature Biotechnology, 2002, 20, 675-681). An equivalent senescence according to the invention means a senescence which is at least 70%, preferably 90%, more preferably at least 95% or above, of that obtained with cells cultivated in a basal medium for the cell type and supplemented with an appropriate serum, usually bovine serum at a 10% concentration (used as a control). Still most preferred is a senescence which occurs at a PDL higher than that observed with cells cultivated in a serum-containing medium. Typically for MRC-5 cells, which are preferred, a senescence of between about PDL60 and about PDL75 is obtained for cells cultivated in the presence of serum as described above.

By "anchorage-dependent animal cells" or "anchorage-dependent human cells" is meant cells that are either established in cell lines or cells that originate from animal or human tissues, which need a solid support for growing and multiplying normally. The solid support is basically a growth surface such as a plastic or glass surface. Example of suitable solid supports are: petri dishes, tissue culture flasks, cells factories, roller bottles or microcarriers. For the purposes of the invention the surface is not coated with any protein from animal origin nor with peptides derived from such proteins. The cells attach and spread out by attachment, i.e. by secretion of their autocrine attachment factors. Preferred anchorage-dependent cells are diploid cells. Non limiting examples of diploid anchorage-dependent cells can be found in ATCC catalogue (WI 38: CCL-75, MRC-5: CCL-171, IMR-90: CCL-186, DBS-FRhL-2: CCL-160, MRC-9: CCL-212) or in NIA catalog (TIG-1 and TIG-7, developed for the NIA Aging Cell Repository, TIG-1 repositary number AG06173; IMR-91:I91L). Preferred cells are MRC-5, WI-38, FRhL-2, MRC-9 and the most preferred cell line is MRC-5.

"Medium substantially free from" is used in reference to a medium, including a fresh and a conditioned medium, which is devoid of serum and of any exogenous components of primary animal origin (such as BSA for example). Such a fresh medium or conditioned medium may contain traces of exogeneous components of secondary animal origin. By "medium free of components from animal origin" is meant a medium which is devoid of serum and of any exogenous components of both primary animal origin (such as BSA for example) and secondary animal origin. Exogenous components from primary animal origin comprise for example components from bovine (including calf), human (such as human serum albumin—HSA) or porcine origin. Components from secondary animal origin are defined as components which are, at one of their manufacturing steps, in contact with a product of animal origin. In particular, frequently used components from secondary animal origin are the recombinant growth factors such as insulin, EGF and FGF and IGF-1. These recombinant growth factors, which may be produced in *E. coli*, are in contact with bovine or porcine components used for fermentation feeding and/or for enzymating cleavages. Traces of components from secondary animal origin are in the range of less than 1%, preferably less than 0.5%, more preferably less than 0.01%, most preferably less than 0.001%, still most preferably absent (0%). Basal serum-free media and animal origin component-free media are commercially available or can be prepared by mixing each of the individual components. They are suitably supplemented with growth factors of non-animal origin. According to the present invention, preferably a medium is used which is totally free from exogenous components of animal origin. Although a medium completely free of exogenous components of animal origin is a preferred embodiment, all said components can be replaced by secondary animal origin components (such as growth factors, wheat peptone, amino acids, protease, etc as recited above) without any impact on the performance of the process.

By "animal origin" or "animal-derived" is meant mammals, e.g. humans, as well as non-mammalian animals such as insects, fish, birds, amphibians and reptiles.

The term "exogeneous" is intended to mean a component of non-animal origin which has been added to the medium, as opposed to a component, referred to as "endogenous", which has been secreted by the cell. In comparison therefore, the term "endogenous" refers to a component which is synthetised and secreted (autocrine secretion) by the cell to contribute to its attachment, spreading and growth on the appropriate substrate (fibronectine, collagen, proteoglycans, growth factors . . . ) (M. R. Koller & E. T. Papoutsakis, Bioprocess Technol., 1995, 60, 61-110).

Preferably the cell culture medium is devoid of exogeneous components of primary animal origin and comprises at least one exogenous growth factor of non-animal secondary origin, preferably at least two, more preferably at least three or more growth factors. Suitably the cell culture medium comprises at least one exogeneous growth factor of non-animal secondary origin selected from the list consisting of: EGF, FGF, tri-iodo-L tyronine and hydrocortisone and at least one of IGF-1 and/or Insulin of non-animal secondary origin. Suitably the culture medium comprises a combination of EGF, FGF, tri-iodo-L tyronine and hydrocortisone of non-animal secondary origin and at least one of IGF-1 and/or Insulin of non-animal secondary origin. The term "growth factor" refers to a protein, a peptide, or a polypeptide, or a complex of polypeptides, including cytokines, that are necessary to the cell growth, that can be produced by the cell during the cultivation process, and that can effect itself and/or a variety of other neighbouring or distant cells, for example by promoting cell attachment and growth. Some, but not all, growth factors are hormones. Examplary growth factors are insulin, insulin-like growth factor (IGF), including IGF-1, epidermal growth factor (EGF), fibroblast growth factor (FGF), including basic FGF (bFGF), granulocyte-macrophage colonstimulating factor (GM-CSF), granulocyte colony-stimulating factor (G-CSF), transforming growth-factor alpha (TGF alpha), platelet-derived growth factors (PDGFs), nerve growth factor (NGF), keratinocyte growth factor (KGF), VEGF, transforming growth-factor beta (TGF beta), interleukin-8 (IL-8), interleukin 6 (IL-6), tri-iodo-L tyronine and hydrocortisone. Preferred growth factors include for example EGF, FGF (preferably bFGF), IGF-1 or Insuline, tri-iodo-L tyronine and hydrocortisone, and can be used either alone or, preferably, in combination. A preferred culture medium contains non-animal derived EGF, FGFb, IGF-1 or Insuline, tri-iodo-L tyronine and hydrocortisone. Still more preferably all components, such as those listed in Table 3, of the cell culture medium according to the invention are of non-animal primary and secondary origin.

In a still preferred embodiment, the culture medium additionally contains a non-animal derived protein hydrolysate, preferably a plant or yeast derived protein hydrolysate. By "protein hydrolysate" or "protein peptone" is meant, as well understood in the art, a purified preparation of a protein hydrolysate or crude fraction thereof, which is therefore protein-free. The term protein-free is intended to mean free of any functionally active protein, but may not exclude, however, non-functional peptides as may originate precisely from protein hydrolysates. A particularly suitable hydrolysate fraction contains wheat peptone protein hydrolysate, e.g. an enzymatic digest composed of peptides from a range of up to 10 000 daltons with a majority of 80% of the peptides between 300 to 1000 daltons. When present, the concentration of protein hydrolysate in the culture medium is between 0 and 10 g/L, when present preferably between 1 and 5 g/L, especially preferably 2.5 g/L. Specifically the protein hydrolysate is derived from plant (e.g. rice, corn, wheat, soya, pea, cotton, potato) or yeast. A preferred plant protein hydrolysate according to the invention is a wheat peptone protein hydrolysate.

The cell culture medium according to the invention alternatively refers to a "fresh medium", a "conditioned medium", or a mixture of both media. A "fresh medium" refers to any cell culture medium, either commercially available or prepared from each of the individual components, that has not been used to cultivate any cells. According to a preferred aspect of the invention, a fresh medium is meant to refer to a commercially available medium or a medium prepared from individual components as described above. This is, according to the invention, which is devoid of primary origin animal components and has been supplemented with at least one exogenous growth factor of non-animal secondary origin as described hereinabove, and optionally, but preferably, with a protein hydrolysate of non-animal origin such as wheat protein hydrolysate.

A "conditioned medium" is intended to mean a medium that has been used by one cell culture and is reused by another. This conditioned medium includes the release of endogenous growth stimulating substances, endogenous attachment factors and specific endogenous nutrients by the first culture.

It is thus another aspect of the invention to provide for a method for producing a conditioned culture medium comprising combining the fresh culture medium according to the invention with animal or preferably human anchorage-dependent cells to generate a conditioned culture medium.

Unless otherwise specified, the fresh medium, the conditioned medium and the mixture of both media will be referred to as "culture medium".

Table 2 shows the concentration range, and the preferred concentration of growth factor(s) and protein hydrolysate as added in the fresh medium. Accordingly, the concentration of growth factors, when present, in a suitable cell culture medium according to the invention is as defined in Table 2.

TABLE 2

| Growth factor | Preferred concentration (mg/liter) | Concentration range (mg/liter) |
|---|---|---|
| EGF | 0.005 | 0.00001-0.3 |
| FGFb | 0.003 | 0.00001-0.1 |
| T3 (triodo L-tyronine) | 0.066 | 0-1 |
| Hydrocortisone | 1 | 0-10 |
| IGF-1 | 0.1 | 0.00001-5 |
| or insulin | 5 | 0.1-1000 |
| Wheat peptone hydrolysate | 2500 | 0-10000 |

It will be understood that, depending on the cell-type cultured and the performance to be achieved, the fresh culture medium according to the invention may be optionally further supplemented with ingredients classically found in culture media and of non-animal origin. Suitable ingredients are, for example, amino acids (including non essential), vitamins, nucleotides/nucleosides, fatty acids, antibiotics and oxidation stabilisers, which are all from non-animal origin.

Suitable fresh media are animal-free standard media such as DMEM-based (high-glucose Dulbecco's Modified Eagle's Media), MEM (Minimum Essential Medium Eagle), Medium 199, RPM-I 1640, all commercially available from, among others, Life-technologies-Gibco-BRL, BioWittaker, Sigma-Aldrich, and further adequately supplemented with growth factor(s) and optionally with a protein hydrolysate of non-animal origin as taught above. The skilled man will understand that the starting medium will need to be selected according to the cell-type being cultured. A preferred commercially available fresh medium is Ultra-MEM, available from BioWhittaker (cat. no 12-745F). Alternatively, depending on the cell type to be cultivated, the fresh medium is an animal-free medium prepared from each of the individual components, and comprises (list non-exhaustive) a source of carbohydrates, inorganic salts ingredients, trace of elements, amino acids (including non essential), vitamins, nucleotides/nucleosides, fatty acids, antibiotics, oxidation stabilisers and water, suitably supplemented with non-animal origin exogeneous growth factor(s) and optionally but preferably with non-animal origin protein hydrolysate as taught above. An example of a basic composition of such a medium is given in Example I and Table 3.

Said media are suitable for the cultivation of animal, such as mammalian or preferably human cells, in particular anchorage-dependent animal, such as mammalian or preferably human cells, preferably anchorage-dependent diploid cells, which represents another aspect of the invention.

In a preferred aspect of the invention, there is also provided a method for producing animal or preferably human anchorage-dependent cells, preferably diploid cells, in a culture medium according to the invention, said method comprising:
a) seeding the cells in said culture medium, and letting the cells adhere to the substrate;
b) harvesting the conditioned medium resulting from step a), and detaching the cell layer from its substrate and dissociating cells with a protease of non-animal origin, thereby forming a cell suspension;
c) inoculating in said culture medium the suspension of cells of step b), in a culture device comprising an adhesion support allowing cell attachment;
d) growing the cells in the same culture medium;
e) optionally repeating steps b) to d).

Optionally the method comprises the step of freezing the cells harvested from the step b), to produce a cell bank.

Optionally the protease used in step b) is inactivated after treatment.

Depending on the cell type and on the performance of the cell culture process to be achieved, the skilled man will understand that the culture medium used, especially in steps a) and c), may alternatively be a fresh medium or a conditioned medium originating from a previous culture or a mixture of fresh and conditioned medium. Within the mixture, the ratio between the fresh culture medium and the conditioned culture medium is between 1:0 (100% fresh medium) and 0:1 (100% conditioned medium). The conditioned medium represents preferably from 0 to about 75% of the total volume of medium. A preferred ratio between fresh culture medium and conditioned culture medium is 1:1 (50% fresh/50% conditioned), a still more preferred ratio is between around 7:1 (87.5% fresh/12.5% conditioned) and 1:7, and a most preferred ratio is between around 3:1 (75% fresh/25% conditioned) and 1:3, and the most preferred ratio is at 3:1 (75% fresh/25% conditioned). The preferred ratios are preferably maintained throughout the culture process at every change of medium.

The protease is from a non-animal origin, that is to say the protease is not purified from an animal source. The protease may be from recombinant origin, but is preferably from bacterial, yeast or plant origin, suitably from non-animal secondary origin. A protease from recombinant origin is intended to mean any protease which is produced by recombinant DNA techniques, and involving the use of a micro-organism, e.g. bacteria, virus, yeasts, plants, etc, for its production. Preferred proteases include: cysteine endopeptidase; neutral fungal protease (from *A. oryzae*); neutral bacterial protease (from *Bacillus subtilis*) (described in Brocklehurst, K. et al., Cysteine proteinases. In *New Comprehensive Biochemistry* Vol. 16, *Hydrolytic Enzymes*; Neuberger, A. & Brocklehurst, K., eds, pp. 39-158 (1987) Elsevier, Amsterdam); serine proteases, such as trypsin-like protease (such as rProtease, from Invitrogen, 3175 Staley Road, Grand Island, N.Y. 14072. Supplier catalogue number 02-106) or recombinant trypsin (such as Trypzean, a recombinant trypsin produced in corn, Prodigen, 101 Gateway Blvd, Suite 100 College Station, Tex. 77845. Manufacturer code: TRY). Proteases from the trypsin-like protease family are commonly found in prokaryotes, animals and viruses, surprisingly so far not found in plants. These enzymes participate in diverse physiological processes, the best known among them are digestions, fertilisation, blood clotting cascade and developmental processes. It is thought that they diverged from a common ancestral protein. These enzymes have been extensively described in the literature (A. J. Greer, "Comparative modelling methods—application to the family of mammalian serine proteases" Proteins, Vol. 7, p 317-334, 1990) and can be divided into different families bases on their structure (A. Sali & T. Blundell, "definition of general topological equivalence in protein structures" J. Mol. Biol., 212, p 403-428, 1990). A suitable protease is a serine protease such as recombinant trypsin or trypsin-like protease. A preferred protease is a neutral fungal protease or a neutral bacterial protease. A more preferred protease according to the invention is a cysteine endopeptidase. A particularly preferred cysteine protease is from vegetal origin. Preferred cysteine endopeptidase from vegetal origin are selected from the group consisting of: ficin (the major proteolytic component of the latex of fig, *Ficus glabrata*) (Liener, I. E. & Friedenson, B. Methods Enzymol, 1970, 19, 261-273), stem bromelain (extracted from the stem of the pineapple plant, *Ananas comosus*), actinidin (from the kiwi fruit or Chinese gooseberry *Actinidia chinensis*) and papain (from latex of the papaya *Carica papaya* fruit). Among the cysteine proteases, ficin is especially preferred.

The protease may be used in any suitable concentration so as to ensure an efficient cell dissociation (individualised cells) within a reasonable detachment time.

The process of producing diploid anchorage-dependent cells is better understood with regard to the steps as illustrated in Example II. In brief, the cell layer originates from cells thawed and seeded for cell culture or from a previous subculture, in a culture medium according to the invention. Then, in a first step, for cell detachment, the medium of the anchorage-dependent cell culture is removed and kept to be used as conditioned medium for the inoculation step. The cell layer, preferably washed, is detached and dissociated in individualised cells by using a protease solution and shaking the flask. When cells are detached and individualised, the cell suspension is collected and can be used for cell inoculation or cell banking. Optionally, when the activity of the protease is toxic for the culture of the cell line, it can be inhibited with an appropriate protease inhibitor. In a second step, for cell inoculation, cells are seeded in the new flasks at the usual cell densities applied for the cell line produced. Then, culture medium, preferably a mixture of fresh culture medium and conditioned medium is added to the new flasks. In a third step, for cell growth, new cell cultures are incubated at the same temperatures and in the same atmospheres as those applied in the usual processes used for the cell line production. An optional fourth step can be applied for cell banking, after step 1 (cell detachment) and instead of steps 2 (cell inoculation) and 3 (cell growth). It is carried out by freezing cells in the medium free of animal-origin components supplemented with the usual animal origin-free cryoprotectant used for the cell line freezing (usually DMSO and methycellulose).

Usually, cells have to be adapted to the growth in a medium free of exogeneous animal-derived components, following a predetermined strategy including several cultures with decreasing concentrations of said components, before their culture in a medium totally free of components of exogenous animal origin (Chandler J P., Am Biotechnol Lab 1990, 8, 18-28). This adaptation steps is required to ensure the usual cell growth and the typical cell morphology.

It has now been found that a process for producing cells according to the invention does not require any adaptation steps before cultivating cells in the medium free of components of exogenous animal origin and that the senescence of the cells is not affected by the absence of this adaptation step. This is another advantage of the invention. In fact, the usual cell growth and the typical cell morphology are maintained for a number of generations (Population Doubling) required to reach the Population Doubling Level (PDL) equal to two third of the PDL at which the senescence of the cells is observed. Preferably, the usual cell growth and the typical cell morphology are maintained for a number of generations (Population Doubling) required to reach the Population Doubling Level (PDL) at which the senescence of the cells is observed. The senescence of the cells is observed at a PDL equivalent to what is observed in usual processes containing animal origin components. For example, for MRC-5 cells coming from a Master Cell Bank (PDL 13) and cultivated in a medium according to the invention, the usual cell growth and the typical cell morphology are maintained during more than 50 generations (Population Doubling) after what the senescence of the cells is observed.

Accordingly the present invention also provides for a cell line, preferably a animal such as mammalian, more preferably a preferably human diploid anchorage-dependent cell line adapted for growth in a culture medium according to the invention. By "adapted" is meant that the typical cell growth and cell morphology are maintained for a number of generations similar to those observed with classical media containing animal-derived components, or alternatively that the senescence is not observed significantly sooner that observed with classical media. Further, the present invention also provides for a cell line, preferably an animal such as mammalian, more preferably a human diploid anchorage-dependent cell line adapted for production of a biologically active product, preferably a virus, in a culture medium according to the invention.

Accordingly, in another embodiment, the present invention accordingly also provides for a method of producing an animal, such as mammalian or preferably human, diploid anchorage-dependent cell culture for recombinant protein or virus production in a culture medium according to the invention, said method comprising passaging said cell culture with a protease as defined above. In particular, anchorage-dependent cells, typically diploid cells, are seeded at low density in a nutrient medium substantially free from exogenous components of animal origin, and after they have multiplied to form a confluent layer or multilayer, they are detached to form a suspension and reseeded at low density again. Preferably the protease used to detach and passage the cells is from a non-animal origin or from a recombinant origin, is selected from the group consisting of: a cystein endopeptidase, a neutral fungal protease, a neutral bacterial protease or a trypsin-like protease. Suitable proteases are trypsin-like protease, such as Trypzean or recombinant trypsin such as rProtease or cystein endopeptidase, more preferably ficin, stem bromelain and actinidin. Among the cysteine proteases, ficin is especially preferred.

In a preferred embodiment, the invention relates to a process for the production of viruses in animal such as mammalian or preferably human anchorage-dependent cells, preferably diploid cells, in a cell culture medium according to the invention:
a) infecting the cells with the virus
b) propagating the viruses, and
c) harvesting the viruses.

Optionally the harvested virus is submitted to one or more purification steps. It is a further aspect of the present invention to provide for a virus produced as herein described and formulated, as an immunogenic composition such as a vaccine, in admixture with a pharmaceutically acceptable carrier, excipient and/or adjuvant.

Depending on the cell type and on the performance of the viral production process to be achieved, the skilled man will understand that the culture medium used to seed the cells in step a) may alternatively be a fresh medium or a conditioned medium originating from a previous culture or a mixture of fresh and conditioned medium. Preferably, for optimal viral production, the ratio between fresh culture medium and conditioned culture medium is between 1:0 (100% fresh medium) and 0:1 (100% conditioned medium). The conditioned medium represents preferably from 0 to about 75% of the total volume of medium. Preferred ratio between fresh culture medium and conditioned culture medium is 1:1 (50% fresh/50% conditioned), still more preferably around 7:1 (87.5% fresh/12.5% conditioned) and most preferably around 3:1 (75% fresh/25% conditioned). A ratio between fresh culture medium and conditioned culture of 1:0 (100% fresh medium) is particularly preferred. The medium used to infect cells and propagate virus may be identical to the growth culture medium, more preferably it comprises 25% w/v EGF, 25% w/v bFGF and 25% w/v T3, and is optionally further supplemented with 20% w/v protein hydrolysate, preferably wheat peptone E1 (Organotechnie SA, France). Still most preferably the medium does not contains any protein hydrolysate.

The process of viral production is better understood with regard to the steps as illustrated in Example III.

In brief, in a first step, for viral infection, the anchorage-dependent cells, cultured according to the process and in a medium according to the invention, are infected with the appropriate virus at the same Multiplicity Of Infection as the one applied in the usual processes used for the virus production. In a second step, for viral propagation, infected cells are incubated at the same temperature and in the same atmosphere as those routinely applied in the usual processes applied for the virus production. In a third step, the virus is harvested after the same propagation time as the one applied in the usual processes used for the virus production. The method of virus harvest is according the method routinely applied in the processes for the virus harvest. For general culture conditions applied to viral production, see Hepatitis A virus culture process (WO 95/24468), Hepatitits A virus vaccines (WO 94/06446; A. Hagen J., 2000, Bioprocess Engineering 23, 439-449).

Examples of viruses and human viral vaccines that can be produced using the medium and the process according to the present invention include live, attenuated, inactivated, recombinant modified viruses. In particular, attenuated viruses for vaccine use that can be propagated on anchorage-dependent cells include, but are not limited to: adenoviridae (i.e. adenovirus 149), herpesviridae (i.e. herpesvirus HSV, cytomegalovirus CMV, Varicella Zoster virus VZV, Epstein-Barr virus EBV), flaviviridae (i.e. dengue virus, Hepatitis C virus HEV, Japanese encephalitis virus, Yellow fever virus), Poxyiridae (i.e. Cowpox virus, Monkeypox virus, vaccinia virus, Variola virus), Picornaviridae (i.e. echovirus, coysackieviruses, Hepatitis A virus, Polioviruses, Rhinoviruses), reoviridae (i.e. rotavirus, Colorado tick fever virus), togaviridae (i.e. Eastern equine encephalytis virus, Rubella virus), hepadnaviridae (i.e. Hepatitis B virus), Retroviridae (i.e. Immuno deficiency viruses HIV/SIV, paramyxoviridae (i.e. Measles virus, Mumps virus, Parainfluenza viruses, Respiratory Syncytial virus RSV), rhabdoviridae (i.e. Rabies virus, Vesicular Stomatitis virus), Orthomyxoviridae (i.e. influenza viruses), unclassified viruses (i.e. Hepatitis E viruse, Hepatitis delta virus), astroviridae (i.e. astrovirus), coronaviridae (i.e. coronavirus), arenaviridae (i.e. Junin virus), Bunyaviridae (i.e. rift valley fever virus). In another embodiment, the production of viral vaccines using the process according to the invention include the production of recombinant proteins expressed in adherent cells. Preferred anchorage-dependent cells include for example AGMK, VERO, MDCK (canine epithelial kidney cell), CEF (Chicken, Embryo Fibroblast) and CHO (chinese ovary) cells, and more particularly preferred cells are anchorage-dependent diploid cells such as for example MRC-5, WI-38, TIG-1, TIG-7, FRhL-2, MRC-9, IMR-90 and IMR 91. MRC-5 is a particularly preferred cell line. The process according to the invention has proven successful for the production of hepatitis A virus, Mumps virus and VZV.

According to a preferred aspect of the invention, cells infected with any of the following viruses are preferred: hepatitis, especially HAV, polio virus, HSV, especially HSV-1 and HSV-2, CMV, EBV, rubella virus, paramyxoviridae (i.e. Measles virus, Mumps virus, Parainfluenza viruses, Respiratory Syncytial virus RSV), VZV.

On average, 15 generations are required to start a master cell bank and 10 generations are required to produce a working cell bank. At least approximately 15 generations are required in order to carry out an average batch culture on the 400 L scale. Starting with an anchorage-dependent cell line and using the medium according to the present invention, it is possible to follow the same plan to prepare a master cell bank (MCB) with approximately 15 generations and a working cell bank (WCB) with approximately 10 generations, and hence a culture with approximately 15 generations under conditions developed with the medium free from exogenous components of animal-origin.

The present invention also contemplates the use of the culture medium as herein above described for the cultivation of cells, preferably diploid anchorage-dependent cells, more preferably eukaryotic cells, most preferably animal, such as mammalian, or preferably human cells. It is also an object of the invention to provide a cell culture that comprises the culture medium according to the invention and the cells, preferably diploid anchorage-dependent cells, more preferably eukaryotic cells, most preferably animal, such as mammalian or preferably human cells.

The present invention further relates to a virus population obtainable by the method as herein defined. It further relates to a method to produce a viral vaccine, comprising admixing said virus population with a pharmaceutically acceptable carrier, excipient or adjuvant.

FIGURE LEGENDS

FIG. 1. Cell density during MRC-5 cells senescence test using ficin and bromelain proteases for cell detachment and using the medium as defined in Example I.1.

Figure 2:
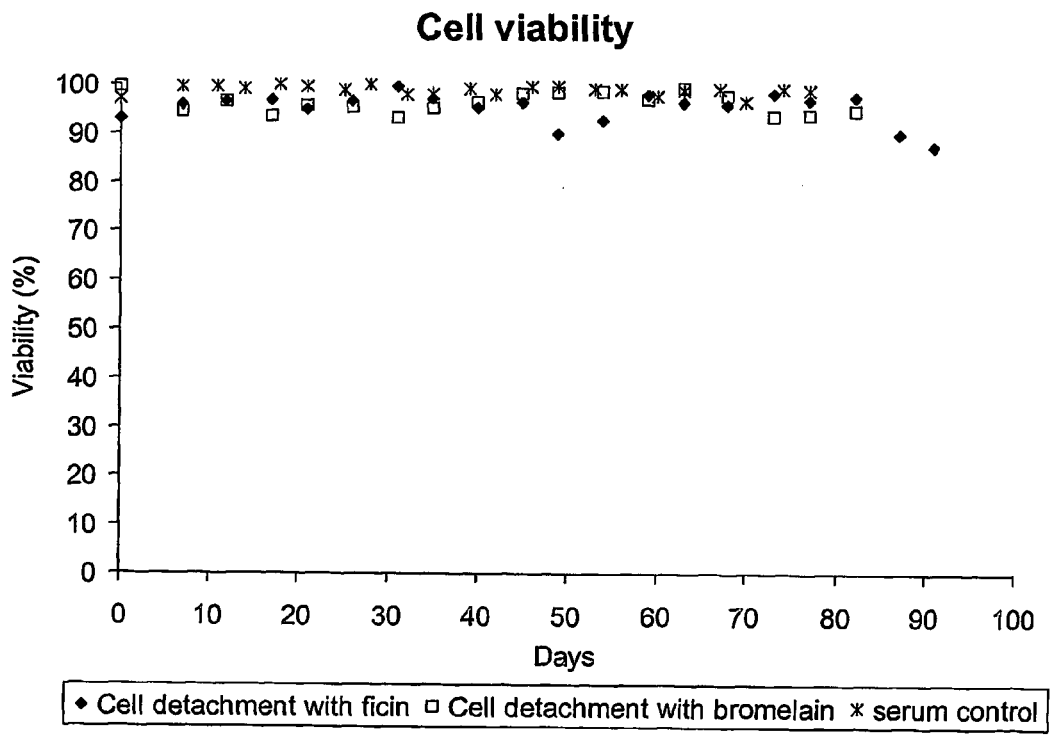

FIG. 2. Cell viability during MRC-5 cells senescence test using ficin and bromelain protease for cell detachment and using the medium as defined in Example I.1.

Figure 3:
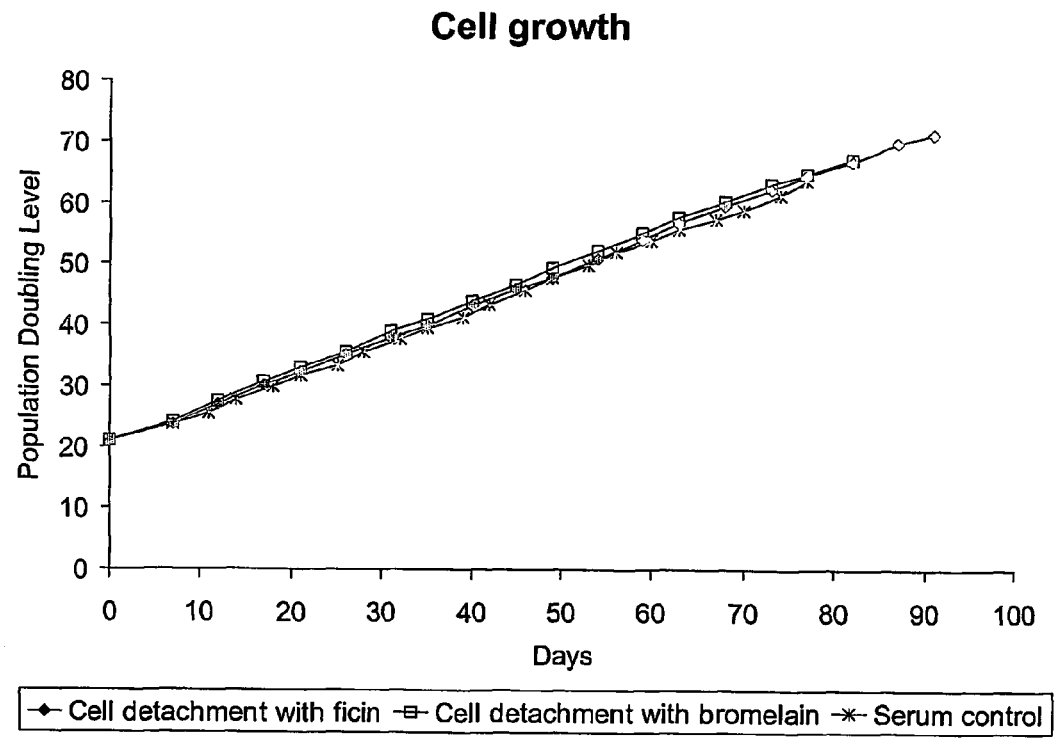

FIG. 3. Cell growth during MRC-5 cells senescence test using ficin and bromelain protease for cell detachment and using the medium as defined in Example I.1.

Figure 4:
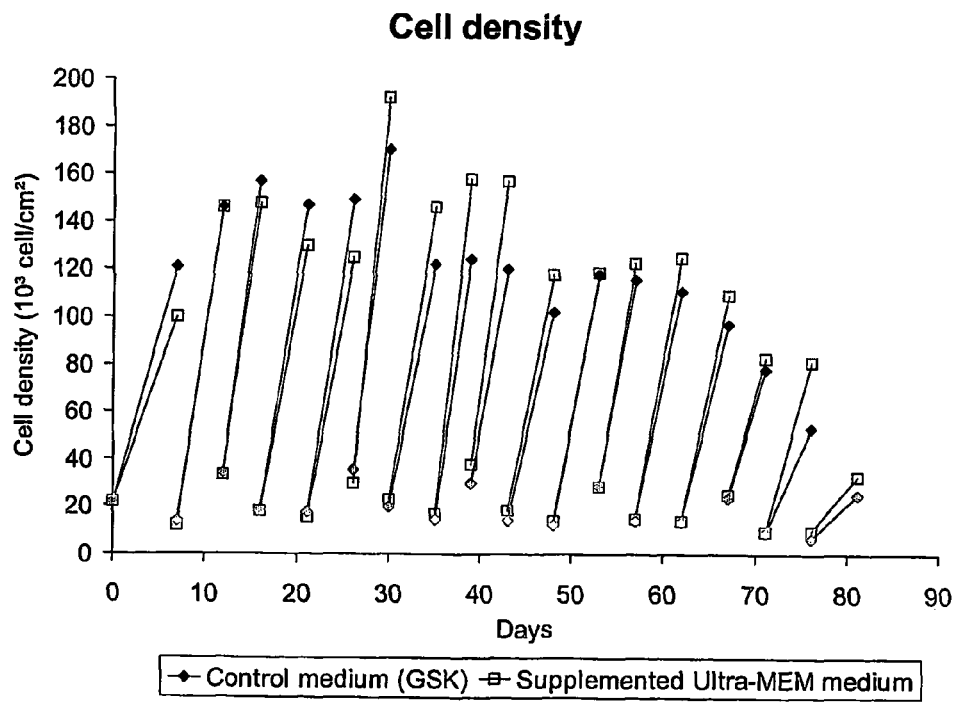

FIG. 4. Comparison of Cell density during MRC-5 cells senescence test obtained with the media as defined in Example I.1 (individual components) and Example I.2 (supplemented ultra-MEM medium).

Figure 5:
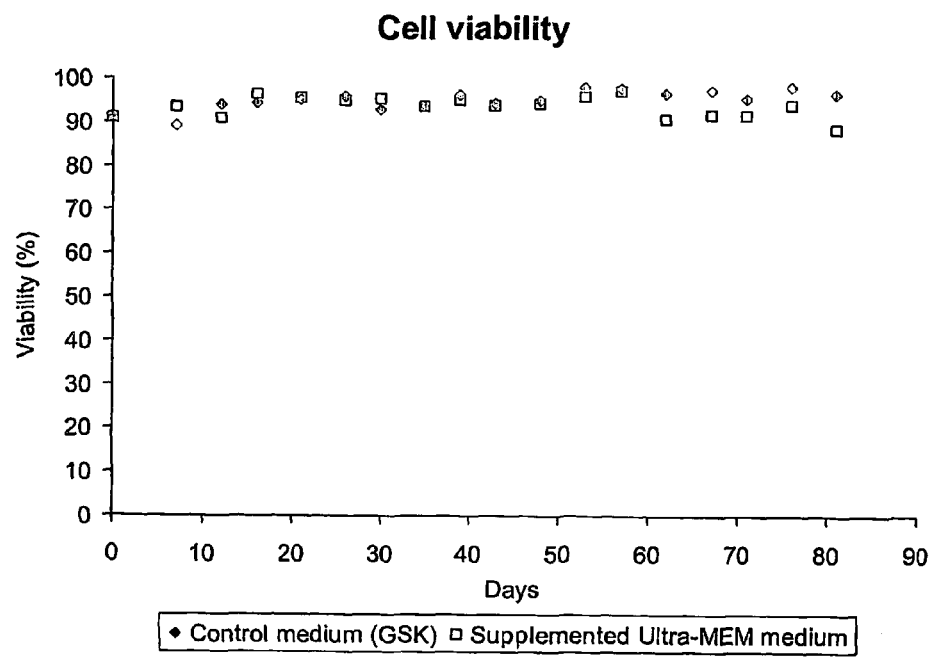

FIG. 5. Cell viability during MRC-5 cells senescence test obtained with the media as defined in Example I.1 (individual components) and Example I.2 (supplemented ultra-MEM medium).

Figure 6:
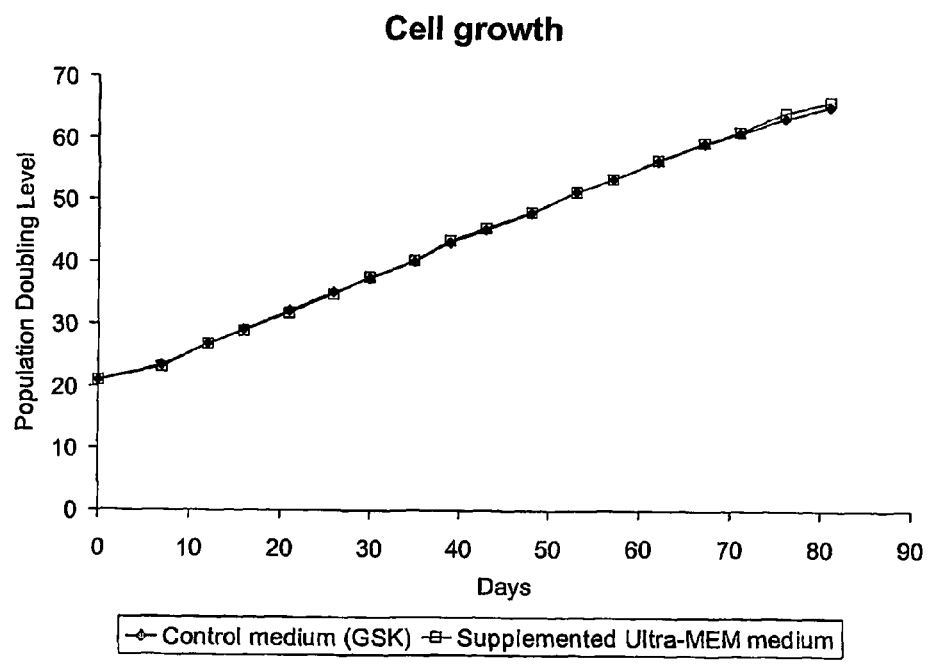

FIG. 6. Cell growth during MRC-5 cells senescence test obtained with the media as defined in Example I.1 (individual components) and Example I.2 (supplemented ultra-MEM medium).

Figure 7:
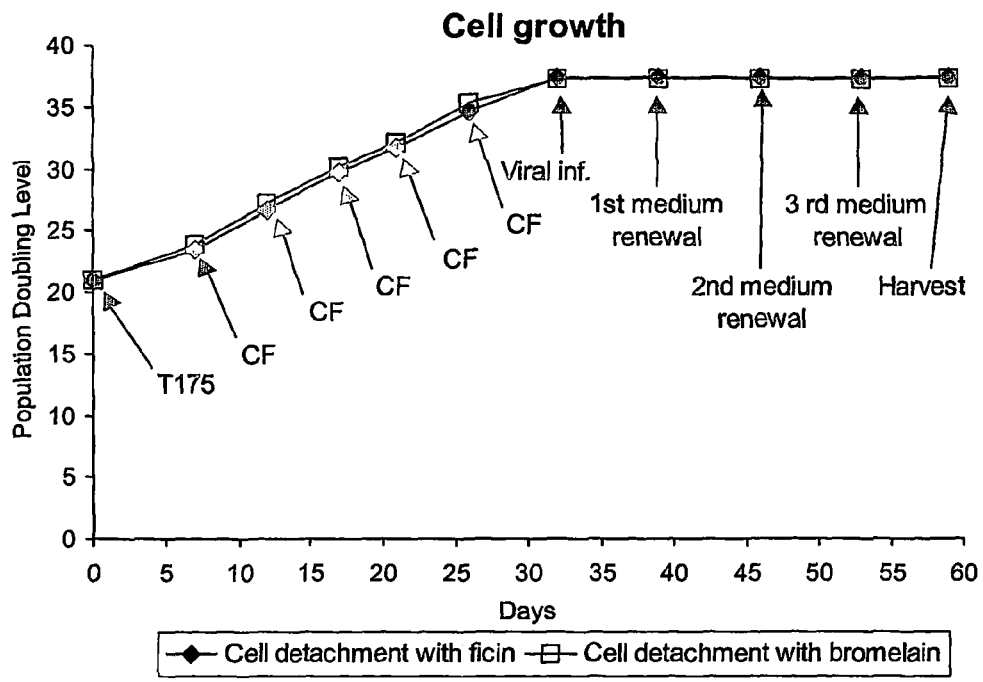

FIG. 7. HAV production on MRC-5 cell multiplied by using ficin and bromelain protease for cell detachment.

Figure 8:
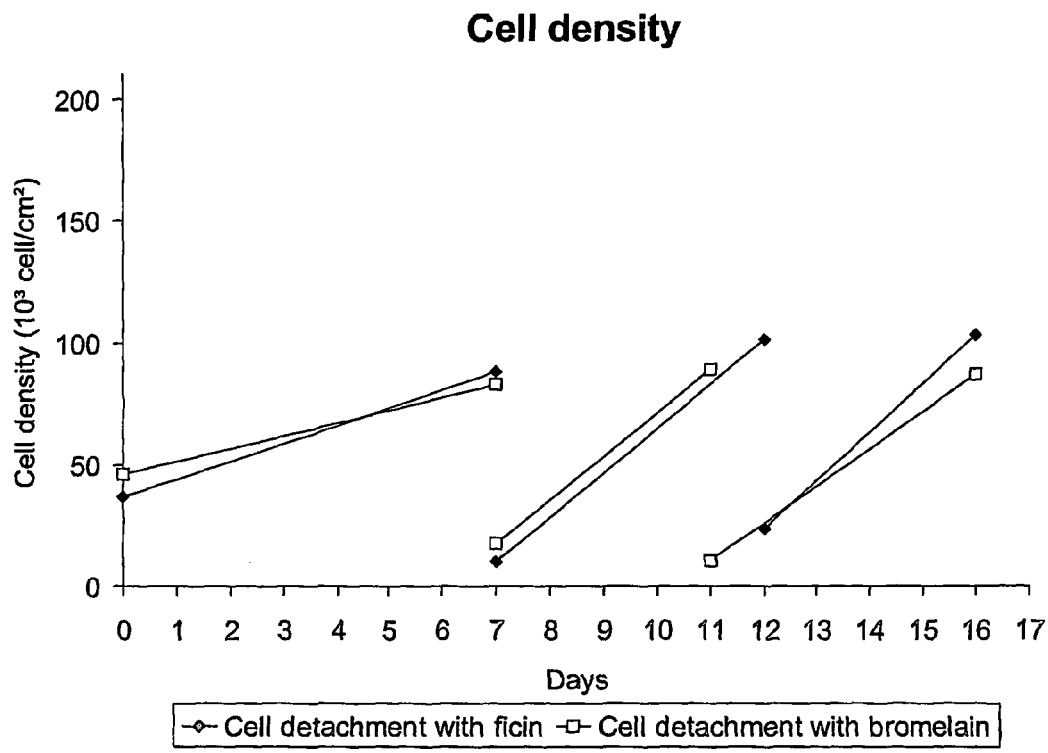

FIG. 8. Cell density during cell banking of MRC-5 cells multiplied by using ficin and bromelain protease for cell detachment.

Figure 9:
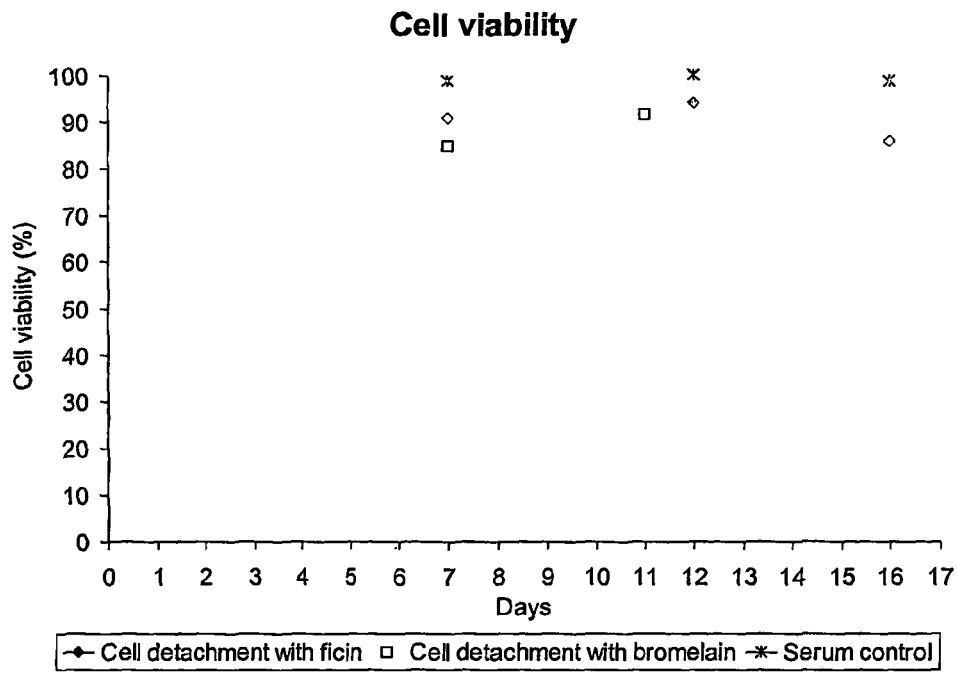

FIG. 9. Cell viability of during cell banking of MRC-5 cells multiplied by using ficin and bromelain protease for cell detachment.

Figure 10:
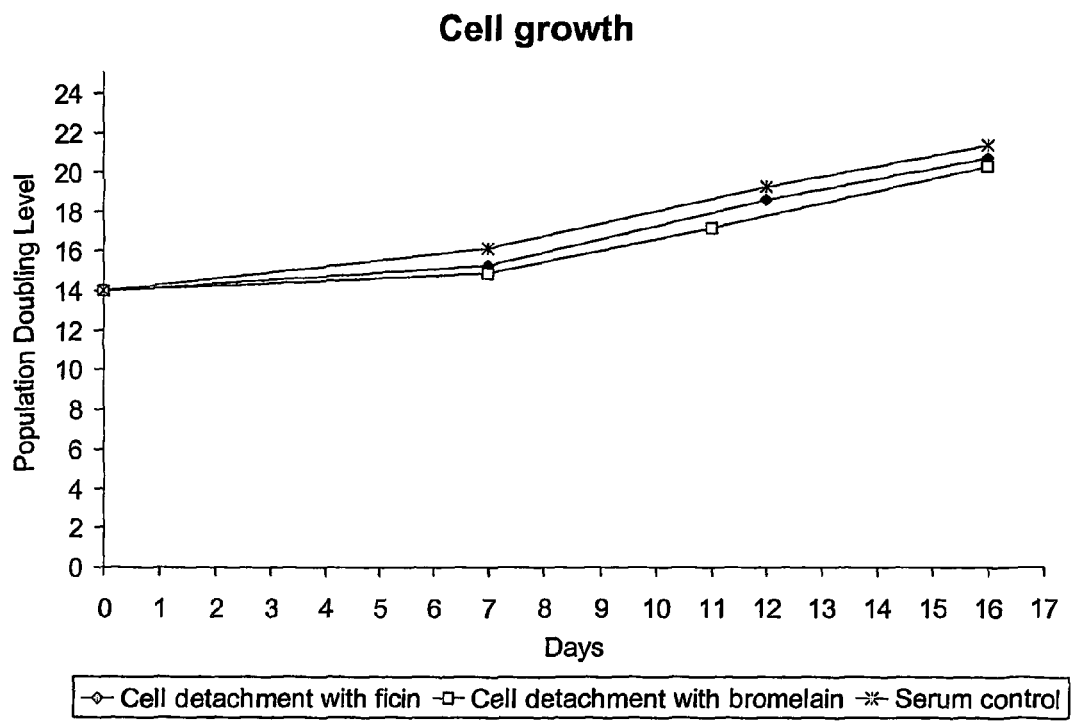

FIG. 10. Cell growth during cell banking of MRC-5 cells multiplied by using ficin and bromelain protease for cell detachment.

Figure 11:
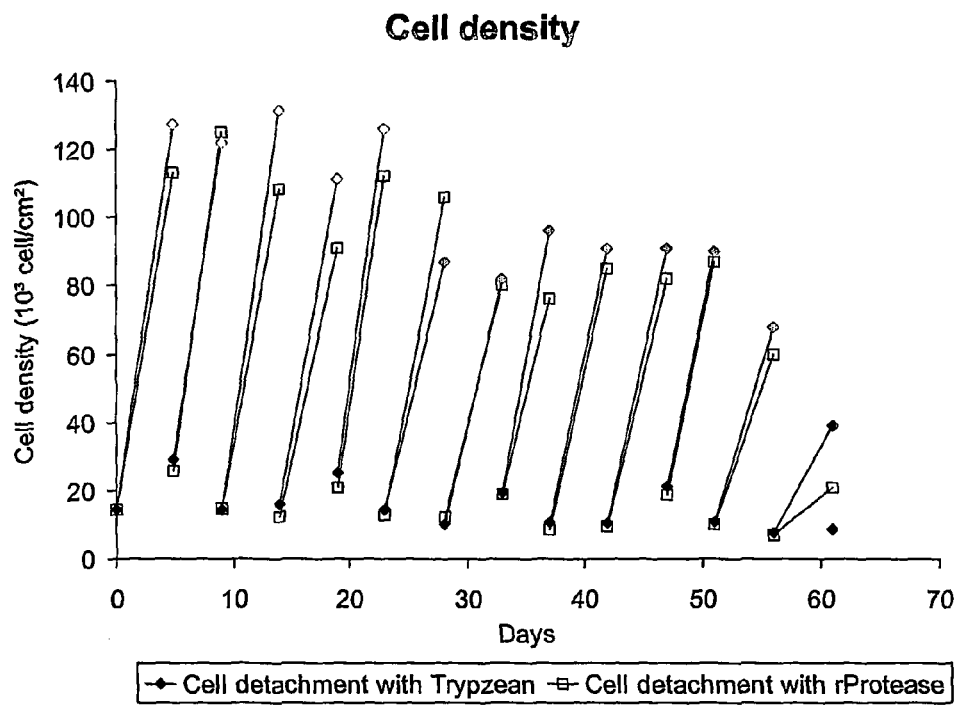

FIG. 11. Cell density during cell banking of MRC-5 cells multiplied by using Trypzean (Prodigen) or rProtease (Invitrogen) for cell detachment.

Figure 12:
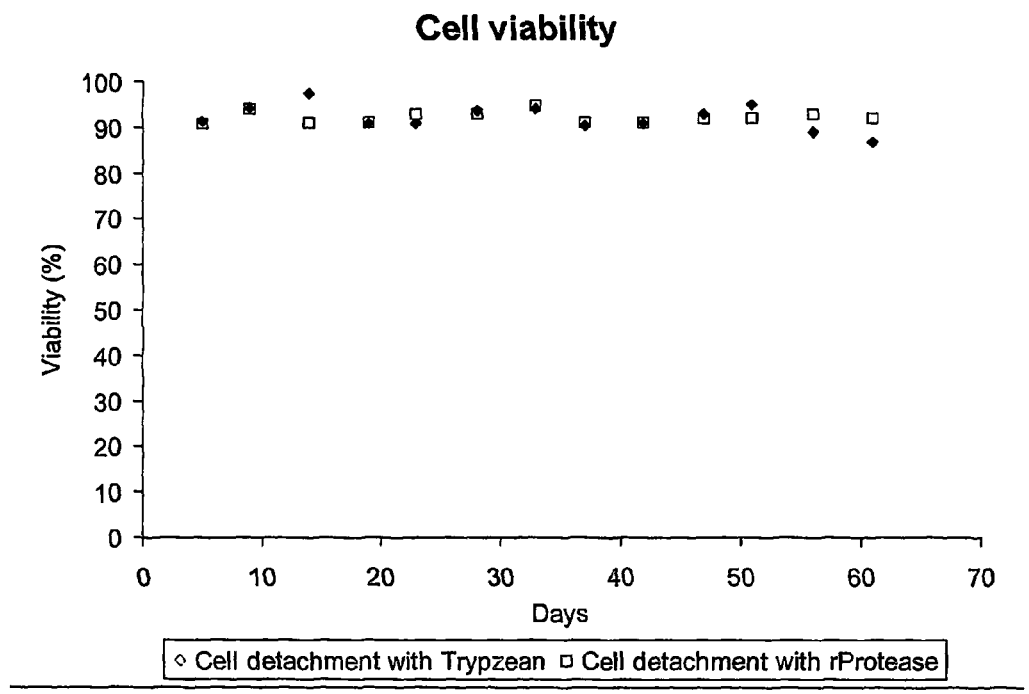

FIG. 12. Cell viability of during cell banking of MRC-5 cells multiplied by Trypzean (Prodigen) or rProtease (Invitrogen) for cell detachment.

Figure 13:
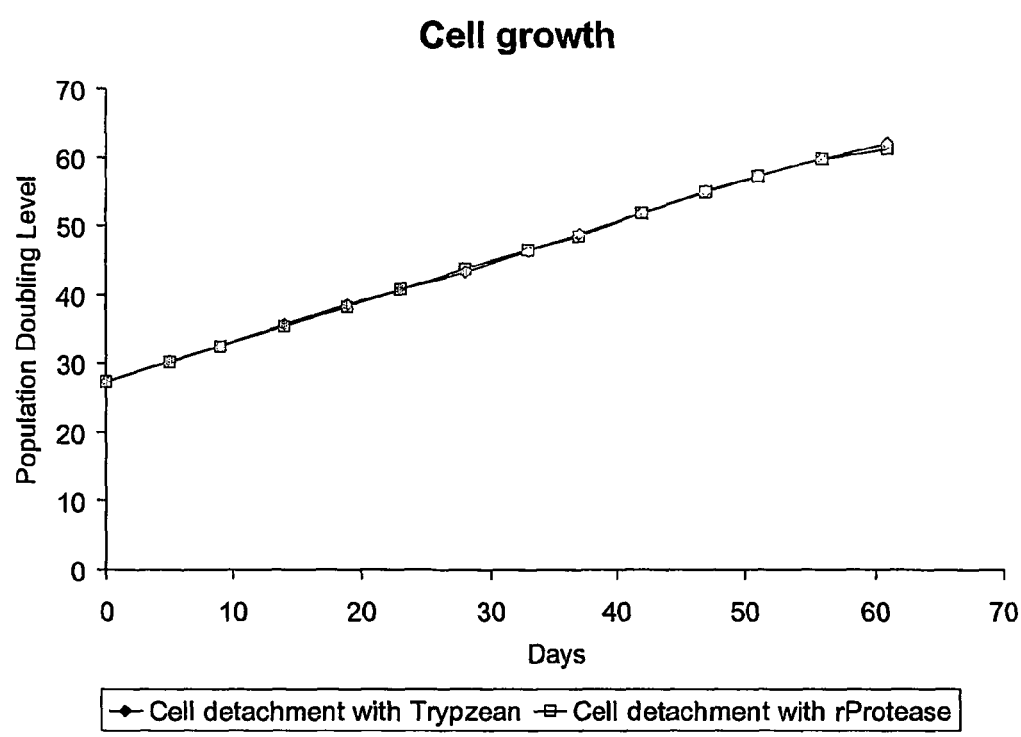

FIG. 13. Cell growth during cell banking of MRC-5 cells multiplied by Trypzean (Prodigen) or rProtease (Invitrogen) for cell detachment.

The invention will be further described by the following, non limiting, examples.

EXAMPLE I

I.1. Preparation of a Fresh Medium from Individual Components

An examplary advantageous fresh culture medium comprises all or most of the common ingredients as listed in Table 3. According to the invention it may be suitably supplemented with the growth factors and protein hydrolysate as listed in table 2.

TABLE 3

Medium free from components of animal origin

| Component | Concentration ranges mg/L | Preferred concentration ranges mg/L | Preferred concentration mg/L |
|---|---|---|---|
| $NaH_2PO_4 \cdot H_2O$ | 60-280 | 80-150 | 99 |
| $Na_2HPO_4$ | 20-400 | 25-50 | 35 |
| NaCl | 5000-8000 | 6000-7000 | 6760 |
| KCl | 180-600 | 250-400 | 349 |
| $AgNO_3$ | 0.000005-0.00004 | 0.000010-0.000060 | 0.000017 |
| $AlCl_3 \cdot 6H_2O$ | 0.000001-0.001 | 0.000008-0.000080 | 0.000012 |
| $Ba(C_2H_3O_2)_2$ | 0.000001-0.002 | 0.00002-0.00003 | 0.0000255 |
| $CaCl_2$ | 100-760 | 150-250 | 155 |
| $CdCl_2 \cdot 2\frac{1}{2}H_2O$ | 0.000001-0.03 | 0.000009-0.00003 | 0.0000187 |
| $CoCl_2 \cdot 6H_2O$ | 0.000001-0.003 | 0.000001-0.00003 | 0.0000238 |
| $Cr_2(SO_4)_3 \cdot XH_2O$ (±15 $H_2O$) | 0.000003-0.0004 | 0.0000005-0.000008 | 0.0000066 |
| $CuSO_4 \cdot 5H_2O$ | 0.00001-0.006 | 0.00009-0.0008 | 0.000637 |
| $Fe(NO_3)_3 \cdot 9H_2O$ | 0.005-1 | 0.1-0.5 | 0.3773 |
| $FeSO_4 \cdot 7H_2O$ | 0.02-2 | 0.1-0.4 | 0.20433 |
| $GeO_2$ | 0.000001-0.0008 | 0.00001-0.0001 | 0.000053 |
| $H_2SeO_3$ | 0.0001-0.02 | 0.0009-0.004 | 0.0016 |
| $Na_2SeO_3$ | 0.001-0.02 | 0.009-0.015 | 0.01 |
| KBr | 0.0000001-0.0003 | 0.0000009-0.000003 | 0.0000012 |
| KI | 0.0000001-0.00009 | 0.000001-0.000004 | 0.0000017 |
| $MgCl_2$ | 5-150 | 10-50 | 14 |
| $MgSO_4$ | 20-150 | 50-100 | 72 |
| $MnSO_4 \cdot H_2O$ | 0.000001-0.005 | 0.00001-0.00009 | 0.0000596 |
| NaF | 0.00001-005 | 0.000009-0.00009 | 0.000042 |

TABLE 3-continued

| Medium free from components of animal origin | | | |
|---|---|---|---|
| Na2SiO3.9H2O | 0.001-0.2 | 0.01-0.1 | 0.07 |
| NaVO3 | 0.00001-0.2 | 0.0001-0.0009 | 0.0003 |
| (NH4)6Mo7O24.4H2O | 0.00001-0.002 | 0.00009-0.0009 | 0.00062 |
| NiSO4.6H2O | 0.000001-0.0002 | 0.000009-0.00009 | 0.000065 |
| RbCl | 0.000001-0.0008 | 0.000009-0.00009 | 0.0000121 |
| SnCl2.2H2O | 0.00001-0.0009 | 0.000009-0.00009 | 0.0000552 |
| ZnSO4.7H2O | 0.01-0.6 | 0.09-0.4 | 0.2107 |
| ZrOCl2.8H2O | 0.00001-0.005 | 0.000009-0.00005 | 0.0000322 |
| L-Alanine | 5-50 | 10-25 | 14.43 |
| L-Arginine.HCl | 60-500 | 100-150 | 106.5 |
| L-Asparagine.H2O | 2-180 | 2-50 | 3.675 |
| L-Aspartic Acid | 5-90 | 10-50 | 17.96 |
| L-Cystein HCl.H2O | 0.1-30 | 1-20 | 8.6583 |
| L-Cystine.2HCl | 25-130 | 25-50 | 28.0721 |
| L-Glutamic Acid | 6-50 | 20-35 | 36.4364 |
| Glycine | 7-60 | 15-50 | 33.6924 |
| L-Histidine.HCl.H2O | 15-70 | 20-50 | 26.2052 |
| L-Isoleucine | 10-200 | 20-100 | 46.2413 |
| L-Leucine | 30-200 | 50-100 | 58.31 |
| L-Lysine.HCl | 30-240 | 50-100 | 79.07 |
| L-Methionine | 2-60 | 10-25 | 15.7976 |
| L-Phenylalanine | 2-45 | 10-45 | 29.6352 |
| L-Proline | 2-45 | 10-45 | 28.0623 |
| L-Serine | 2-50 | 10-40 | 25.1174 |
| L-Threonine | 20-150 | 20-100 | 40.9444 |
| L-Tryptophan | 3-25 | 5-15 | 9.3198 |
| L-Tyrosine.2Na.2H2O | 5-150 | 10-100 | 55.7718 |
| L-Valine | 5-150 | 20-100 | 38.05 |
| D-Calcium Pantothenate | 0.01-3 | 0.9-2 | 1.1025 |
| Folic Acid | 0.01-20 | 0.9-5 | 1.3083 |
| Pyridoxal.HCl | 0.001-4 | 0.001-0.02 | 0.01225 |
| Vitamine A (Rétinol) Acétate | 0.01-0.1 | 0.01-0.09 | 0.0686 |
| Vitamine B (Nicotinic Acid) | 0.001-0.1 | 0.009-0.09 | 0.03725 |
| Vitamine B1 (Thiamine).HCl | 0.001-20 | 0.8-5 | 1.0682 |
| Vitamine B2 (Riboflavine) | 0.001-5 | 0.01-0.5 | 0.1127 |
| Vitamine B6 (Pyridoxine).HCl | 0.001-5 | 0.8-3 | 1.00695 |
| Vitamine B12 (Cyanocobalamine) | 0.001-5 | 0.7-1 | 0.3332 |
| Vitamine C (Ascorbic Acid) | 0.001-30 | 0.01-0.09 | 0.0245 |
| Vitamine D2 (Calciférol) | 0.001-0.1 | 0.01-0.07 | 0.049 |
| Vitamine E (alpha-Tocophérol) | 0.0001-0.1 | 0.001-0.009 | 0.0049 |
| Vitamine H (D-Biotine) | 0.0001-0.5 | 0.001-0.009 | 0.006615 |
| Vitamine K3 (Ménadione) | 0.0001-0.5 | 0.001-0.009 | 0.0049 |
| Thymidine | 0.01-5 | 0.09-2 | 0.1764 |
| Adenosine 5' Triphophate disodium | 0.01-10 | 0.1-5 | 0.49 |
| Adenosine-5-phophate | 0.001-0.2 | 0.01-0.1 | 0.098 |
| 2-Deoxyribose | 0.01-10 | 0.1-5 | 0.245 |
| D-Glucose | 1000-4000 | 1500-3000 | 2364 |
| Ribose | 0.01-0.9 | 0.09-0.5 | 0.245 |
| Lipoic acid (Thioctic acid) | 0.001-0.7 | 0.01-1 | 0.05145 |
| Linoleic acid | 0.001-0.3 | 0.01-0.1 | 0.02058 |
| Adénine.H2SO4.H2O | 1-10 | 2-6 | 4.9 |
| Choline Chloride | 0.1-10 | 2-6 | 4.6452 |
| Ethanolamine HCl | 0.1-6 | 1-4 | 1.9 |
| Ethanolamine | 0.0001-0.001 µl/L | 0.0001-0.0009 | 0.0006 µl/L |
| Glutathione | 0.001-0.1 | 0.009-0.08 | 0.0245 |
| Guanine.HCL | 0.01-0.6 | 0.09-0.3 | 0.147 |
| Hypoxanthine | 0.01-15 | 0.09-5 | 0.17346 |
| Hypoxanthine Na | 0.01-6 | 0.09-5 | 1.1711 |
| i-Inositol | 0.6-20 | 2-10 | 6.1495 |
| Na Pyruvate | 10-150 | 60-120 | 82 |
| Nicotinamid/Niacinamide | 0.1-15 | 0.9-4 | 1.00205 |
| Para-aminobenzoic acid | 0.001-0.3 | 0.01-0.1 | 0.0245 |

TABLE 3-continued

| Medium free from components of animal origin | | | |
|---|---|---|---|
| Phospho-Ethanolamine | 0.1-3 | 0.9-2 | 1.2 |
| Putrescine.2HCl | 0.001-0.09 | 0.01-0.06 | 0.03969 |
| Sodium acetate | 10-50 | 15-35 | 24.5 |
| Thymine | 0.01-0.4 | 0.05-0.3 | 0.147 |
| Uracile | 0.01-0.4 | 0.05-0.3 | 0.147 |
| Xanthine Na | 0.01-0.5 | 0.08-0.3 | 0.16856 |
| Glutamine | 50-300 | 100-300 | 292.2 |
| NaHCO3 | 1000-2500 | 1000-1500 | 1170 |
| HEPES | 1700-7000 | 3000-6800 | 6670 |
| Ferric fructose stock solution | 50 µl/L to 1000 µl/L | 80-200 µl/L | 166.7 µl/LL |
| Plant or yeast derived hydrolysate, preferably wheat peptone | 0-10000 | 1000-4000 | 2500 |

| Ferric fructose stock solution | |
|---|---|
| Component | Concentration* mg/L |
| FeCl3.6H20 | 2420 |
| D-Fructose | 160000 |

*In Table 3 above, an iron complex (ferric fructose) is also used as an iron source in addition to an inorganic iron.

I.2. Preparation of a Fresh Medium from a Commercially Available Medium Suitably Supplemented Commercially available medium: Ultra-MEM cat. No 12-745F (Reduced Serum Medium, Protein-free Basal Medium, without L-Glutamine) available from BioWhittaker.

The basal medium formulation is free from components of animal-origin but is classically designed, according to the manufacturer's instruction, to be supplemented with a small quantity of serum (such as less than 10%) and other additives (ITES=Insulin (animal origin)+Transferrin (animal origin)+Ethanolamine+Selenium). The medium has been used in the absence of the recommended supplements from animal origin (serum and ITES).

This medium has been supplemented with the following ingredients, all free from components of primary and secondary animal origin:
1. IGF-1:0.1 mg/L
2. EGF: 0.005 mg/L
3. bFGF: 0.003 mg/L
4. Triiodo-L-tyronine (T3): 0.066 mg/L
5. Wheat Peptone E1:2.5 g/L and further with
6. Ferric Fructose: 0.1667 ml/L
7. Sodium Pyruvate: 0.055 g/L The following ingredients have also been added in order to optimise the culture process carried out in the absence of components of animal-origin:
  Glutamine: 0.2922 g/L
  Glucose: 0.33 g/L
  Selenium (Na2SeO3): 0.01 mg/L
  Ethanolamine: 0.0006 µl/L MRC-5 cells from an animal-free cell bank (PDL 21) are thawed and cultivated according to the process disclosed in Example II and IV, using the medium described above and the following sub-culture scheme:
  D7: cell inoculation by ratio 1/8 in 100 ml of growth medium composed of 12.5% of conditioned medium
  D12: cell inoculation by ratio 1/4 in 100 ml of growth medium composed of 25% of conditioned medium
  D16: cell inoculation by ratio 1/8 in 100 ml of growth medium composed of 12.5% of conditioned medium
  D21: repeat the scheme starting at D7

Cells are cultivated in 175 cm$^2$ T-flasks until senescence (±PDL 65) during±3 months (e.g. 80 days). In this procedure, the cell inoculum is not fixed to a targeted cell density. Cell countings, carried out for control, show that the cell inoculum densities are included between 9000 cells/cm$^2$ and 40000 cells/cm$^2$ before senescence is observed. The MRC-5 cells reached the PDL66 after 81 days of culture with a cell growth rate of 0.57 PDL/day after what senescence was observed. These results, illustrated in FIGS. 4, 5 and 6, are equivalent to what is observed with a medium prepared from individual components as illustrated in section 1.2 which leads to senescence at around PDL 65 after 81 days and cell growth rate of around 0.56 PDL.

In parallel, cells will derived from this culture are used to produce HAV according to the process described in Example III, using the same medium as described here above except that the EGF, bFGF and T3 concentrations are reduced to 25% of the concentration present in the cell growth culture medium and except that the wheat peptone concentration is reduced to 0.5 g/L. Harvest of virus is carried out 2 months after the start of the culture.

EXAMPLE II

Process for Producing Animal or Human Anchorage-Dependent Cells in a Culture Medium Substantially Free of any Components from Animal Origin.

Step 1: Cell Detachment

The culture medium of an anchorage-dependent cell culture, grown in cell culture flask, is removed and kept in a sterile container. This recovered medium is considered as a conditioned medium and will be used for the inoculation of the cells. The cell layer is washed twice with a Phosphate Buffer Saline (PBS) supplemented with EDTA. A target of about 0.04 grams to about 1 grams of EDTA per liter of PBS and preferably about 0.2 grams/L is desirable.

Once the cell layer is washed, a sufficient volume of the protease solution is added so that the to whole cell layer is covered. A targeted volume of about 0.01 ml/cm$^2$ to 2 ml/cm$^2$ and preferably 0.0333 ml/cm$^2$ is desirable. This protease solution is prepared by dissolution of the enzyme in a PBS supplemented with EDTA. A target of about 0.02 grams to about 0.5 grams of EDTA per liter of PBS and preferably about 0.1 grams/L is desirable. The quantity of protease added to the PBS/EDTA is the one required to generate a solution with a sufficient proteolytic activity to achieve an efficient cell detachment. The cell detachment is considered as efficient when a majority of the cells are detached from the flask and when cell aggregates are dissociated in individualized cells after a desirable targeted time of about 5 minutes to about 30 minutes and preferably about 12 minutes. The enzymatic activity of some proteases that can be used on anchorage-dependent cells is given in the following list for example, but not limited to:

A targeted enzymatic activity of about 5.5 pUPABA/ml to about 550 μUPABA/ml and preferably about 55 pUPABA/ml is desirable for Ficin (one unit of PABA is the activity of the enzyme which hydrolyzes 1 μmole of Na-benzoyl-DL-arginine -p-nitroaniline/minute at 37° C. (Methods in Enzymology Vol XIX Proteolytic enzymes p261-284).

A targeted enzymatic activity of about 0.001 Gelatin Digested Units (GDU)/ml to about 0.1 GDU/ml and preferably about 0.01 GDU/ml is desirable for Bromelain (one unit of GDU activity is the activity of the enzyme which liberates 1 mg of amino acids from a determined substrate of gelatine in the condition fo the assay—(same reference as above).

A targeted enzymatic activity corresponding to a protein quantity of about 12.5 μg/ml (1.25 μg/ml to about 125 μg/ml and preferably about 12.5 μg/ml is desirable for neutral fungal protease from $A.$ $oryzae$ (according to the manufacturer, Lyven Zac Normandial, 11 avenue du Pays de Caen 14460 Colombelles, France).

A targeted enzymatic activity corresponding to a protein quantity of about 150 μg/ml (15 μg/ml to about 1.5 mg/ml and preferably about 150 μg/ml is desirable for neutral bacterial protease from $B.$ $subtilis$ (according to the manufacturer, Lyven Zac Normandial, 11 avenue du Pays de Caen 14460 Colombelles, France).

A targeted enzymatic activity of about 100 USP/ml to 0.1 USP/ml and preferably 1 USP/ml is desirable for Trypzean (according to the manufacturer Prodigen, 101 Gateway Blvd, Suite 100 College Station, Tex. 77845. Manufacturer code :TRY).

A targeted dilution of the stock solution of about 3 times to 300 times and preferably 30 times is desirable for the rProtease (according to the supplier Invitrogen, 3175 Staley Road, Grand Island, N.Y. 14072. Supplier catalogue number 02-106).

When cell detachment is observed, the flask is gently shaked and the cell suspension is collected in a sterile container. In order to recover a maximum of cells, the flask is rinsed with fresh culture medium which is collected in the same sterile container. Cell suspension is then ready for the cell inoculation step or the cell banking step.

Step 2: Cell Inoculation

Anchorage-dependent cells obtained after cell detachment described in the step 1 can be inoculated in new flasks following these instructions:

Cells are inoculated at the same cell densities as those applied in the usual processes for anchorage-dependent cell cultures with animal-origin components. For example, MRC-5 cells are inoculated at a targeted cell density of about 5000 cell/cm$^2$ to about 40000 cell/cm$^2$ and preferably between 7500 cell/cm$^2$ and 25000 cell/cm$^2$.

The volume of the growth medium added into the flask, after cell inoculation, is the same as the one added in the usual processes for anchorage-dependent cell culture with animal-origin components. The growth medium is composed of a mixture of fresh culture medium and conditioned medium. The conditioned medium is the cell culture medium recovered at the beginning of the cell detachment step (see step 1). The quantity of conditioned medium added to the fresh medium is dependent on the cell line inoculated. A general target of 0% to about 75% of conditioned medium is desirable. To give an example, for MRC-5 cell culture, a target of about 10% to about 35% of conditioned medium is preferably desirable and a target of about 0.025 ml/cm$^2$ to about 3 ml/cm$^2$ of culture medium added into the flasks is preferably desirable.

Step 3: Cell Growth

Anchorage-dependent cells inoculated in cell culture flask are incubated at the same temperatures as those applied in the usual processes for anchorage-dependent cell cultures with components of animal-origin. For example, a target temperature of about 30° C. to about 40° C. and preferably at 37° C. is desirable for MRC-5 cells incubation.

Anchorage-dependent cells inoculated in cell culture flask are incubated in the same atmospheres as those applied in the usual processes for anchorage-dependent cell cultures with animal-origin components. For example MRC-5 cells can be incubated with or without $CO_2$ control and with or without relative humidity control.

Step 4: Cell Banking

Anchorage-dependent cells obtained after cell detachment described in the step 1 can be frozen, for cell banking, following the same procedures as those applied in the usual processes for anchorage-dependent cell cultures with animal-origin components, except the following points:

Cells must be frozen in the medium free of animal-origin components, supplemented with the same animal origin-free cryoprotectant additives as those used in the usual processes for anchorage-dependent cell freezing with animal-origin components. For example, MRC-5 cells are frozen in the medium free of animal-origin components supplemented with a desirable target of about 2.5% to about 12.5% of DMSO and a desirable target of about 0.01% to about 1% of methylcellulose.

EXAMPLE III

Process for the Production of Viruses in Animal or Human Anchorage-Dependent Cells in a Culture Medium.

Step 5: Viral Infection

Anchorage-dependent cells are infected with the same Multipicity Of Infection (MOI) as those applied in the usual processes for anchorage-dependent cell cultures with animal-origin components. For example, a MOI target of about 0.005 to about 1 is desirable for MRC-5 cells infection by Hepatitis A Virus (HAV). Cells are infected in a medium free of animal-origin components as herein described and supplemented with ingredients according to Table 2. For the viral production, the protein hydrolysate is optional.

Step 6: Viral Propagation

Anchorage-dependent cells infected are incubated at the same temperatures as those applied in the usual processes for viral propagation on anchorage-dependent cell cultures with animal-origin components. For example, a target temperature of about 31° C. to about 33° C. and preferably at 32° C. is desirable for HAV propagation on MRC-5 cells. Anchorage-dependent cells infected are incubated in the same atmospheres as those applied in the usual processes for viral propagation on anchorage-dependent cell cultures with animal-origin components. For example MRC-5 cells infected by HAV can be incubated with or without $CO_2$ control and with or without relative humidity control.

Step 7: Virus Harvest

The time for viral propagation between viral infection of anchorage-dependent cells and virus harvest is the same as the one applied in the usual processes for viral propagation on anchorage-dependent cell cultures with animal-origin components. For example HAV propagation on MRC-5 cells is achieved by about 21-29 days after viral infection.

The method of virus harvest is the same as the one applied in the usual processes for virus harvest on anchorage-dependent cell cultures with animal-origin components. For example, the harvest of HAV produced on MRC-5 cells starts with two washings of the cell layer with a PBS after what the virus is recovered by cell detachment using a PBS supplemented with 0.1 to 1 g/L of EDTA and then cell lysis by freezing.

EXAMPLE IV

MRC-5 Cell Culture Until Senescence Using Ficin Protease for Cell Detachment (See FIGS. 1, 2 and 3)

A small scale procedure for MRC-5 cells senescence testing requires the repeat of the cell production method with the process free of animal-origin components described in the steps 1 to 3, until senescence is observed. MRC-5 cells coming from a cell bank PDL 21: free of components from animal origin are thawed, inoculated in a Nunc T175 $cm^2$ flask with 100 ml of a fresh medium suitably supplemented as described in Table 2 and incubated at 37° C. After seven days, sub-cultures (see steps 1 to 3) are carried out in Nunc T-175 $cm^2$ flask at 37° C., using 4.2 ml of a ficin solution with an enzymatic activity of 45 μUPABA/ml for cell detachment. Sub-culture are carried out according to the following scheme:

D7: cell inoculation by ratio 1/8 in 100 ml of growht medium composed of 12.5% of conditioned medium
D12: cell inoculation by ratio 1/8 in 100 ml of growht medium composed of 12.5% of conditioned medium
D17: cell inoculation by ratio 1/4 in 100 ml of growht medium composed of 25% of conditioned medium
D21: repeat the scheme starting at D7

In this procedure, the cell inoculum is not fixed to a targeted cell density. Cell countings, carried out for control, show that the cell inoculum densities are included between 8000 cells/$cm^2$ and 33000 cells/$cm^2$. The MRC-5 cells reached the Population Doubling Level 71 after 90 days of culture with a cell growth rate of 0.56 PDL/day after what senescence was observed. These results, illustrated in FIGS. 1, 2 and 3, are equivalent to what is observed with a procedure using porcine trypsin for cell detachment and bovine serum (senescence at around PDL 65 after 83 days and cell growth rate of around 0.55 PDUday (Wistrom C, Villeponteau. B. Exp. Gerontol, 1990; 25(2): 97-105)).

EXAMPLE V

MRC-5 Cell Culture Until Senescence Using Bromelain Protease for Cell Detachment (see FIGS. 1, 2 and 3)

This process is similar to the one disclosed in the Example III except the following points:
a bromelain solution with an enzymatic activity of 0.01105 Gelatin Digested Units (GDU)/ml is used for cell detachment instead of the ficin solution.
Sub-culture are carried out according to the following scheme:

D7: cell inoculation by ratio 1/8 in 100 ml of growth medium composed of 12.5% of conditioned medium
D12: cell inoculation by ratio 1/8 in 100 ml of growth medium composed of 12.5% of conditioned medium
D17: cell inoculation by ratio 1/4 in 100 ml of growth medium composed of 12.5% of conditioned medium
D21: repeat the scheme starting at D7

Cell countings, carried out for control, show that the cell inoculum densities are included between 8000 cells/$cm^2$ and 33000 cells/$cm^2$. The MRC-5 cells reached the Population Doubling Level 67 after 82 days of culture with a cell growth rate of 0.56 PDL/day after what senescence was observed. These results, as illustrated in FIGS. 1, 2 and 3, are equivalent to what is observed with a procedure using porcine trypsin for cell detachment and bovine serum (senescence at PDL 65 after 83 days and cell growth rate=0.55 PDL/day (Wistrom C, Villeponteau. B. Exp. Gerontol, 1990; 25(2): 97-105)).

EXAMPLE VI

HAV Production on MRC-5 Cells Multiplied by Using Ficin Protease for Cell Detachment (see FIG. 7)

HAV production in Nunc Cell Factories (CF) with MRC-5 cells cultured by using ficin protease for cell detachment, requires the implementation of the method describe in the steps 5 to 7 of the Example II. MRC-5 cells coming from a cell bank (at PDL 21) free of animal-origin components are multiplied in Nunc T175 $cm^2$ flask then in CF until the Population Doubling Level 36 is reached, by using the method describe in the steps 1 to 3 of the Example I (FIG. 7). MRC-5 cells are infected with HAV stock seed prepared in the medium described in the Table 2 at a target MOI of 0.01. After infection, cells are incubated at 32° C. during 27 days with 3 medium renewals after 7, 14 and 21 days (FIG. 7). HAV harvest is carried out 27 days after infection by starting with two washings of the cell layer with a PBS, then by detaching cells with a PBS supplemented with about 0.2 g/L of EDTA and finally by freezing cells. Antigenic titers of the HAV bulk obtained using this procedure are between 250 and 350 E.L.I.S.A Units (ELU)/0.1 ml. This results are equivalent to what is observed with a procedure using porcine trypsin for cell detachment and bovine serum (HAV Bulk antigenic titers=250 ELU/0.1 ml).

EXAMPLE VII

HAV Production on MRC-5 Cells Multiplied by Using Bromelain Protease for Cell Detachment (see FIG. 7)

This process is similar to the one disclosed in the Example V except that a bromelain solution with an enzymatic activity of 0.01105 Gelatin Digested Units (GDU)/ml is used for cell detachment instead of the ficin solution.

Antigenic titers of the HAV bulk obtained using this procedure are between 250 and 350 E.L.I.S.A Units/0.1 ml. This results are equivalent to what is observed with a procedure using porcine trypsin for cell detachment and bovine serum (HAV Bulk titer ≈250 ELU/0.1 ml).

EXAMPLE VIII

Cell Banking of MRC-5 Cell Multiplied by Using Ficin Protease for Cell Detachment (see FIGS. 8, 9 and 10)

A cell banking procedure for MRC-5 cell multiplied with ficin, requires the repeat of the cell production method with the process free of components from animal origin described in the steps 1 to 3 of the Example I, until the chosen PDL is reached (PDL 21). At this PDL, cells are frozen following the method described in the step 4 of the Example I. MRC-5 cells coming from a cell bank (at PDL 14) containing serum are thawed, inoculated in a Nunc T175 cm² flask with 100 ml of the medium described in the Table 2 and incubated at 37° C. After seven days, sub-cultures (see steps 1 to 3) are carried out in Nunc T-175 cm² flask at 37° C., using 4.2 ml of a ficin solution with an enzymatic activity of 45 pUPABA/ml for cell detachment. Sub-culture are carried out according to the following scheme:
D7: cell inoculation by ratio 1/8 in 100 ml of growth medium composed of 12.5% of conditioned medium
D12: cell inoculation by ratio 1/4 in 100 ml of growth medium composed of 25% of conditioned medium
D16: cell banking using a ratio 1/4

In this procedure, the cell inoculum is not fixed to a targeted cell density. Cell countings results are shown in FIGS. 8, 9 and 10. The MRC-5 cells reached the PDL 21 after 16 days. At this PDL MRC-5 cells are frozen in the medium free of animal-origin components supplemented with 7.5% DMSO and 0.1% of methylcellulose. After thawing, these MRC-5 cells show a viability and a cell growth equivalent to what is observed before freezing (viability of about 90-95% and cell growth rate >0.55 PDL/day) (see FIGS. 1, 2 and 3). This results are equivalent to what is observed with a procedure using porcine trypsin for cell detachment and bovine serum (viability of about 90-95% and cell growth rate=0.55 PDU-day (Wistrom C, Villeponteau. B. Exp. Gerontol, 1990; 25(2): 97-105)).

EXAMPLE IX

Cell Banking of MRC-5 Cell Multiplied by Using Bromelain Protease for Cell Detachment (see FIGS. 8, 9 and 10)

This process is similar to the one disclosed in the Example VII except the following points:
a bromelain solution with an enzymatic activity of 0.01105 Gelatin Digested Units (GDU)/ml is used for cell detachment instead of the ficin solution.
Sub-culture are carried out according to the following scheme:
D7: cell inoculation by ratio 1/4 in 100 ml of growth medium composed of 25% of conditioned medium
D11: cell inoculation by ratio 1/8 in 100 ml of growth medium composed of 12.5% of conditioned medium
D16: cell banking using a ratio 1/4

Cell countings results are shown in FIGS. 8, 9 and 10. The MRC-5 cells reached the Population Doubling Level 21 after 16 days. After thawing, these MRC-5 cells show a viability and a cell growth equivalent to what is observed before freezing (viability of about 90-95% and cell growth rate >0.55 PDUday) (see FIGS. 1, 2 and 3). These results are equivalent to what is observed with a procedure using porcine trypsin for cell detachment and bovine serum (viability of about 90-95% and cell growth rate 0.55 PDL/day (Wistrom C, Villeponteau. B. Exp. Gerontol, 1990; 25(2): 97-105)).

EXAMPLE X

MRC-5 Cell Culture Until Senescence Using Trypzean (Prodigen) or rProtease (Invitrogen) for Cell Detachment A small scale procedure for MRC-5 cells senescence testing is carried out, involving repeating the cell production method with the process free of animal-origin components described in the steps 1 to 3 of Example II, until senescence is observed. MRC-5 cells from a cell culture around PDL 27, free of components from animal origin, are propagated in Nunc T175 cm² using a Trypzean solution with an activity of 1 USP/ml or using a rProtease (Invitrogen) solution (stock solution 30 time diluted in PBS supplemented with EDTA as used for cell detachment, see step 1 Example II), according to the following scheme:
D0: cell inoculation by ratio 1/8 in 100 ml of growth medium composed of 12.5% of conditioned medium
D5: cell inoculation by ratio 1/4 in 100 ml of growth medium composed of 25% of conditioned medium
D9: cell inoculation by ratio 1/8 in 100 ml of growth medium composed of 12.5% of conditioned medium
D14: repeat the scheme starting at D0

In this procedure, the cell inoculum is not fixed to a targeted cell density. Cell countings, carried out for the control sample, show that the cell inoculum densities are between 8000 cells/cm² and 30000 cells/cm². MRC-5 cells reached a PDL superior to 60 after 61 days of culture with a cell growth rate of arround 0.56 PDL/day after what senescence was observed. These results, illustrated in FIGS. 11, 12 and 13, are equivalent to what is observed with a procedure using porcine trypsin for cell detachment and bovine serum (senescence at around PDL 65 after 83 days and cell growth rate of around 0.55 PDL/day (Wistrom C, Villeponteau. B. Exp. Gerontol, 1990; 25(2): 97-105)).

The invention claimed is:

1. A method for culturing diploid anchorage-dependent cells, the method comprising:
   a) seeding diploid anchorage-dependent cells onto a first cell-supporting substrate in a cell culture medium, wherein the cell culture medium is devoid of exogenous components of primary and secondary animal origin, and which comprises:
      i) at least one exogenous growth factor of non-animal origin selected from the group consisting of EGF, FGF, tri-iodo-L tyronine and hydrocortisone,
      ii) at least one exogenous growth factor of non-animal origin selected from the group consisting of IGF-1 and insulin, and
      iii) a wheat protein hydrolysate;
   b) letting the cells adhere to the substrate and multiply;
   c) harvesting the culture medium;
   d) detaching the cells from the substrate and dissociating the cells with a protease of non-animal origin, thereby forming a cell suspension;
   e) inoculating a portion of the cell suspension onto a second cell-supporting substrate in a cell culture medium as defined in step a).

2. The method according claim 1 wherein the cell culture medium used in step a) is fresh medium.

3. The method according to claim 1 wherein the cell culture medium used in step a) is a conditioned medium.

4. The method according to claim 1 wherein the cell culture medium used in step a) is a mixture of conditioned medium and fresh medium.

5. The method according to claim 4 wherein the cell culture medium used in step a) is a mixture of fresh medium and conditioned medium in a ratio (fresh:conditioned) of between 7:1 and 1:7.

6. The method according to claim 4 wherein the cell culture medium used in step a) is a mixture of fresh medium and conditioned medium in a ratio (fresh:conditioned) of between 3:1 and 1:3.

7. The method according to claim 4 wherein the cell culture medium used in step a) is a mixture of fresh medium and conditioned medium in a ratio (fresh:conditioned) of 3:1.

8. The method according to claim 1, wherein the wheat hydrolysate is a wheat peptone protein hydrolysate.

9. The method according to claim 1, wherein the protease of non-animal origin used in step b) is selected from the group consisting of a cysteine endopeptidase, a neutral fungal protease, a neutral bacterial protease and a serine protease.

10. The method according to claim 1, wherein the protease of non-animal origin used in step b) is recombinant trypsin or a trypsin-like protease.

11. The method according to claim 1, wherein the protease of non-animal origin used in step b) is a cysteine endopeptidase selected from the group consisting of ficin, stem bromelain, and actinidin.

12. The method according to claim 1, wherein said cells are human diploid anchorage-dependent cells.

13. The method according to claim 1, wherein the diploid anchorage-dependent cells are MRC-5, WI-38, TIG-1, TIG-7, FRhL-2, MRC-9, IMR-90 or IMR-91 cells.

14. A method of culturing diploid anchorage-dependent cells in a culture medium comprising the step of:
passaging said cell culture with a protease of non-animal origin;
wherein said cell culture is maintained in a cell culture medium which is devoid of exogenous components of primary and secondary animal origin, and which comprises:
i) at least one exogenous growth factor of non-animal origin selected from the group consisting of EGF, FGF, tri-iodo-L tyronine and hydrocortisone,
ii) at least one exogenous growth factor of non-animal origin selected from the group consisting of IGF-1 and insulin, and
iii) a wheat protein hydrolysate.

15. The method according to claim 14, wherein the protease of non-animal is selected from the group consisting of cysteine endopeptidase, a neutral fungal protease, a neutral bacterial protease and a trypsin-like protease.

16. The method according to claim 14, wherein the protease of non-animal origin is a cysteine endopeptidase selected from the group consisting of ficin, stem bromelain, and actinidin.

17. The method according to claim 14, wherein said cells are human diploid anchorage-dependent cells.

18. A method for producing a cell bank of diploid anchorage-dependent cells, the method comprising:
a) seeding diploid anchorage-dependent cells onto a cell-supporting substrate in a cell culture medium, wherein the cell culture medium is devoid of exogenous components of primary and secondary animal origin, and which comprises:
i) at least one exogenous growth factor of non-animal origin selected from the group consisting of EGF, FGF, tri-iodo-L tyronine and hydrocortisone,
ii) at least one exogenous growth factor of non-animal origin selected from the group consisting of IGF-1 and insulin, and
iii) a wheat protein hydrolysate;
b) allowing the cells to adhere to the substrate and multiply;
c) removing the cell culture medium;
d) detaching the cells from the substrate and dissociating the cells with a protease of non-animal origin, thereby forming a cell suspension;
e) adding cell culture medium as defined in step a) and a cryoprotectant of non-animal origin to the cell suspension; and
f) freezing the cell suspension to produce a cell bank.

19. The method according to claim 18, wherein the cell culture medium comprises fresh medium.

20. The method according to claim 18, wherein the cell culture medium comprises conditioned medium.

21. The method according to claim 18 wherein the cell culture medium comprises a mixture of conditioned medium and fresh medium.

22. The method according to claim 21, wherein the cell culture medium used in step a) is a mixture of fresh medium and conditioned medium in a ratio (fresh:conditioned) of between 7:1 and 1:7.

23. The method according to claim 21, wherein the cell culture medium used in step a) is a mixture of fresh medium and conditioned medium in a ratio (fresh:conditioned) of between 3:1 and 1:3.

24. The method according to claim 18, wherein the wheat hydrolysate is a wheat peptone protein hydrolysate.

25. The method according to claim 18, wherein the protease of non-animal origin used in step b) is selected from the group consisting of a cysteine endopeptidase, a neutral fungal protease, a neutral bacterial protease and a serine protease.

26. The method according to claim 18, wherein the protease of non-animal origin used in step b) is selected from the group consisting of ficin, stem bromelain and actinidin.

27. The method according to claim 18, wherein the protease of non-animal origin used in step b) is recombinant trypsin or a trypsin-like protease.

28. The method according to claim 18, wherein the diploid anchorage-dependent cells are MRC-5, WI-38, TIG-1, TIG-7, FRhL-2, MRC-9, IMR-90 or IMR-91 cells.

29. A method for producing a diploid anchorage-dependent cells, the method comprising:
a) seeding diploid anchorage-dependent cells onto a first cell-supporting substrate in a cell culture medium, wherein the cell culture medium is devoid of exogenous components of primary and secondary animal origin, and which comprises:
i) at least one exogenous growth factor of non-animal origin selected from the group consisting of EGF, FGF, tri-iodo-L tyronine and hydrocortisone,
ii) at least one exogenous growth factor of non-animal origin selected from the group consisting of IGF-1 and insulin, and
iii) a wheat protein hydrolysate;
b) allowing the cells to adhere to the substrate and multiply;
c) removing the culture medium;
d) detaching the cells from the substrate and dissociating the cells with a protease of non-animal origin, thereby forming a cell suspension; and
e) inoculating a portion of the cell suspension onto a second cell-supporting substrate in a cell culture medium as defined in step a) to produce a diploid anchorage-dependent cell culture.

30. The method according to claim 29, wherein the cell culture medium used in step a) is a mixture of fresh medium and conditioned medium in a ratio (fresh:conditioned) of between 7:1 to 1:7.

31. The method according to claim 29, wherein the cell culture medium used in step a) is a mixture of fresh medium and conditioned medium in a ratio (fresh:conditioned) of between 3:1 and 1:3.

32. The method according to claim 29, wherein the wheat hydrolysate is a wheat peptone protein hydrolysate.

33. The method according to claim 29, wherein the protease of non-animal origin used in step d) is selected from the group consisting of a cysteine endopeptidase, a neutral fungal protease, a natural bacterial protease and a serine protease.

34. The method according to claim 29, wherein the protease of non-animal origin used in step d) is a cysteine endopeptidase selected from the group consisting of ficin, stem bromelain and actinidin.

35. The method according to claim 29, wherein the protease of non-animal origin used in step d) is recombinant trypsin or a trypsin-like protein.

36. The method according to claim 29, wherein the diploid anchorage-dependent cells are MRC-5, WI-38, TIG-1, TIG-7, FRhL-2, MRC-9, IMR-90 or IMR-91 cells.

* * * * *